(12) United States Patent
Zhang et al.

(10) Patent No.: US 8,192,995 B2
(45) Date of Patent: Jun. 5, 2012

(54) METHOD OF CORRECTION OF PARTICLE INTERFERENCE TO HEMOGLOBIN MEASUREMENT

(75) Inventors: Shuliang Zhang, Miami, FL (US); Jiuliu Lu, Homestead, FL (US); Min Zheng, Pembroke Pines, FL (US); Eric M. Grace, Cooper City, FL (US); Jing Li, Miami, FL (US); Maritza Lavernia, Miami, FL (US); Ted W. Britton, Sunrise, FL (US)

(73) Assignee: Beckman Coulter, Inc., Brea, CA (US)

( * ) Notice: Subject to any disclaimer, the term of this patent is extended or adjusted under 35 U.S.C. 154(b) by 288 days.

(21) Appl. No.: 12/616,273

(22) Filed: Nov. 11, 2009

(65) Prior Publication Data

US 2010/0159605 A1 Jun. 24, 2010

Related U.S. Application Data

(60) Provisional application No. 61/114,294, filed on Nov. 13, 2008.

(51) Int. Cl.
*G01N 33/72* (2006.01)
*G01N 33/48* (2006.01)

(52) U.S. Cl. .......... 436/66; 436/8; 436/10; 436/63; 436/164; 436/174; 436/175; 436/149; 436/150; 422/82.02; 422/82.05; 422/82.09; 422/73; 435/2; 435/29

(58) Field of Classification Search .......... 436/63, 436/66, 164, 174, 175, 149, 150, 8, 10, 17; 422/82.01, 82.02, 82.05, 82.09, 73; 435/2, 435/4, 29, 39
See application file for complete search history.

(56) References Cited

U.S. PATENT DOCUMENTS

| | | | | |
|---|---|---|---|---|
| 5,858,794 A | * | 1/1999 | Malin | 436/66 |
| 6,410,330 B1 | * | 6/2002 | Li et al. | 436/10 |
| 6,632,676 B1 | * | 10/2003 | Crews et al. | 436/18 |
| 6,740,527 B1 | * | 5/2004 | Wong et al. | 436/17 |
| 2003/0096302 A1 | | 5/2003 | Yguerabide et al. | |
| 2006/0203226 A1 | | 9/2006 | Roche et al. | |
| 2007/0054403 A1 | | 3/2007 | Zheng et al. | |
| 2007/0054404 A1 | * | 3/2007 | Huo et al. | 436/66 |

OTHER PUBLICATIONS

International Search Report and the Written Opinion of the International Searching Authority, application No. PCT/US2009/064021, dated Jan. 15, 2010.

* cited by examiner

*Primary Examiner* — Maureen Wallenhorst
(74) *Attorney, Agent, or Firm* — K&L Gates LLP; Louis C. Cullman; Andrew L. Reibman

(57) ABSTRACT

A method of correction of particle interference to hemoglobin measurement of a blood sample on a hematology analyzer is provided. The method includes mixing an aliquot of a blood sample with a lytic reagent to lyse red blood cells and forming a sample mixture; measuring absorbance of the sample mixture at a predetermined wavelength of a hemoglobin chromogen formed in the sample mixture, and obtaining an apparent hemoglobin concentration of the blood sample using obtained absorbance; measuring concentration and size of cellular particles remaining in the sample mixture; removing contribution of the cellular particles to the apparent hemoglobin concentration using the concentration and the size of the cellular particles to obtain a corrected hemoglobin concentration of the blood sample; and reporting the corrected hemoglobin concentration of the blood sample.

23 Claims, 7 Drawing Sheets

| Sample No. | $C_p$ (x10³/µL) (Raw WBC) | Gran% | Lymph% | Mono% |
|---|---|---|---|---|
| 1 | 125.0 | 14.4 | 64.1 | 21.6 |
| 2 | 138.6 | 14.7 | 61.0 | 24.3 |
| 3 | 141.6 | 13.2 | 61.8 | 25.0 |
| 4 | 135.5 | 96.1 | 0.2 | 3.7 |
| 5 | 165.8 | 36.8 | 2.5 | 60.7 |
| 6 | 173.1 | 33.3 | 8.7 | 58.0 |
| 7 | 209.5 | 86.2 | 0.2 | 13.5 |
| 8 | 259.1 | 83.1 | 0.5 | 16.4 |

| | | | |
|---|---|---|---|
| ▲ | Gran | Y= 0.0165X+13.786, | $R^2$=0.9947 |
| ● | Lymph | Y= - 0.0036X+13.94, | $R^2$=0.9905 |
| △ | Gran_Theoretical | Y= - 0.0129X+14.116, | $R^2$=1.000 |
| ○ | Lymph_Theoretical | Y= - 0.0138X+14.125, | $R^2$=1.000 |

METHOD OF CORRECTION OF PARTICLE INTERFERENCE TO HEMOGLOBIN MEASUREMENT

CROSS-REFERENCE TO RELATED APPLICATION

This application is a non-provisional application claiming the benefit under 35 U.S.C. §119(e) of U.S. Provisional Application No. 61/114,294, filed on Nov. 13, 2008, which is incorporated herein by reference in its entirety.

BACKGROUND

1. Field of Invention

This invention relates to hemoglobin measurement of blood samples, and more specifically relates to methods of correction of particle interference to hemoglobin measurement on automated hematology analyzers.

2. Background

Determination of total hemoglobin concentration is indicative of the oxygen-carrying capacity of whole blood. More than 300 abnormal hemoglobins have been discovered upon examination of patients with clinical symptoms and by electrophoretic surveys of a clinically normal population. Many of these abnormalities result in clinical pathologies having altered hemoglobin levels or hemoglobin having an altered ability to bind oxygen.

Commercial hematology analyzers are equipped to measure and report hemoglobin concentration of blood samples. On most hematology analyzers, the process of measuring hemoglobin concentration of a blood sample involves lysing red blood cells in a blood sample and forming a hemoglobin chromogen in the sample mixture, measuring spectrophotometric absorbance of the sample mixture at a predetermined wavelength, and reporting a total hemoglobin concentration of the blood sample.

In the sample mixture used for measuring hemoglobin concentration, red blood cells are lysed to release hemoglobin molecules, other cellular particles such as white blood cells, nucleated red blood cells and platelets remain in the sample mixture, although they may be damaged or shrunk in size. It is known that these cellular particles present in the sample mixture interfere with the spectrophotometric measurement of hemoglobin, because the cellular particles absorb and scatter the incident light used in the measurement. In normal blood samples, white blood cell concentration is typically from $4 \times 10^3/\mu L$ to $9 \times 10^3/\mu L$ and platelet concentration is typically from $200 \times 10^3/\mu L$ to $400 \times 10^3/\mu L$. However, in some pathological conditions, for example, severe lipemia or proteinemia, white blood cell concentration can be higher than $20 \times 10^3/\mu L$ and platelet concentration can be higher than $700 \times 10^3/\mu L$. In some leukocytosis samples, the white blood cell concentration can be substantially higher than $100 \times 10^3/\mu L$. These cellular particles in the sample mixture used for hemoglobin measurement may cause significant overestimation of the hemoglobin concentration. The particle interference has also been encountered with blood samples with a significant amount of hemoglobin S and severe microcytosis/hypochromasia.

Several methods are currently used to prevent, or correct the interference of cellular particles to hemoglobin measurement. In the Clinical and Laboratory Standards Institute (formerly NCCLS) manual reference method, when the absorbance of the sample mixture at 750 nm is $\geq 0.003$, or when the absorbance ratio (absorbance at 540 nm vs. absorbance at 504 nm) is <1.59, it is required to filter the sample mixture through a 0.22 µm filter to remove the particles.

A common practice in clinical diagnosis laboratories, as often recommended by hematology analyzer manufacturers, after the hematology analyzer reports abnormally high white blood cell concentration, the blood sample is analyzed again with a pre-dilution to determine hemoglobin concentration. In this process, the blood sample is diluted by a saline solution, or diluted by a diluent used on the hematology analyzer to reduce the concentration of the particles, for example, to reduce the white blood cell concentration down to below $20 \times 10^3/\mu L$ or a level that the manufacturer recommends. Then, the pre-diluted sample is analyzed again on the instrument to measure hemoglobin. The obtained hemoglobin concentration from the pre-diluted sample is used to calculate the hemoglobin concentration of the blood sample, taking account for the dilution. This method has several disadvantages. The blood sample has to be analyzed twice on the instrument. It is time consuming and requires manual preparation by an operator. The pre-dilution introduces additional errors originated from pipetting the blood and the diluent, and manually mixing the blood prior to and after the dilution. Moreover, for a blood sample that has a low hemoglobin concentration, further dilution reduces accuracy of hemoglobin measurement.

Another known method to correct particle interference to hemoglobin measurement is to measure the absorbance of the sample mixture at two different wavelengths. The first wavelength is in the visible region, for example at 540 nm, which is used to measure the hemoglobin chromogen. The second wavelength is at infra-red region, for example at 800 nm to measure turbidity caused by the cellular particles. The absorbance at the second wavelength is used to correct the measurement at the first wavelength to produce a corrected hemoglobin concentration. A hand-held device using this method is commercially available from HemoCue AB (Ängelholm, Sweden) under the trade name of Hemocue Hb 201+. This device is used for measuring hemoglobin only, not other hematology parameters. In some hematology laboratories, particularly in Europe, after a blood sample has been analyzed on a hematology analyzer and reported to have an abnormally high white blood cell concentration, Hemocue Hb 201+ is then used to measure and report hemoglobin concentration.

Accordingly, there is a need for a method, particularly an automated process on automated hematology analyzers, to correct the interference of cellular particles to the measurement of hemoglobin concentration.

BRIEF SUMMARY

In one aspect, the present invention is directed to a method of correcting particle interference to hemoglobin measurement of a blood sample. In one embodiment, the method comprises mixing an aliquot of a blood sample with a lytic reagent to lyse red blood cells and forming a sample mixture; measuring absorbance of the sample mixture at a predetermined wavelength of a hemoglobin chromogen formed in the sample mixture, and obtaining an apparent hemoglobin concentration of the blood sample using obtained absorbance; measuring concentration and size of cellular particles remaining in the sample mixture; removing contribution of the cellular particles to the apparent hemoglobin concentration using the concentration and the size of the cellular particles to obtain a corrected hemoglobin concentration of the blood sample; and reporting the corrected hemoglobin concentration of the blood sample.

In one embodiment, the contribution of said cellular particles to said apparent hemoglobin concentration is defined as a function of said concentration and a size factor of said cellular particles, and the function further comprises a conversion factor. The corrected hemoglobin concentration is obtained by subtracting the function from the apparent hemoglobin concentration. The size factor of the cellular particles can be defined by mean volume, mean cross-section area, mean diameter, or a combination thereof, of the cellular particles in the sample mixture.

In a further embodiment, the method further comprises comparing the obtained concentration of the cellular particles to a predetermined criterion, and when the concentration of cellular particles exceeds the predetermined criterion, then initiating the correction process.

Additionally, the method of the present invention further provides corrected mean corpuscular hemoglobin (MCH) and corrected mean corpuscular hemoglobin concentration (MCHC). In one embodiment, the method further comprises mixing another aliquot of the blood sample with a diluent to form another sample mixture; measuring concentration and mean cell volume of red blood cells in the another sample mixture; obtaining a corrected mean corpuscular hemoglobin (MCH) using the corrected hemoglobin concentration and the concentration of the red blood cells; and obtaining corrected mean corpuscular hemoglobin concentration (MCHC) using the corrected hemoglobin concentration, the concentration of the red blood cells and the mean cell volume.

In a further aspect, the present invention is directed to an automated process for correction of particle interference to hemoglobin measurement of a blood sample on a hematology analyzer. The process comprises passing a first sample mixture portion through a light path, measuring absorbance of the first sample mixture portion at a predetermined wavelength of a hemoglobin chromogen formed in the first sample mixture portion to obtain an apparent hemoglobin concentration of the blood sample, and storing the apparent hemoglobin concentration in a first memory; passing a second sample mixture portion through a particle measurement device, counting the number of cellular particles in the second sample mixture portion to obtain the concentration of the cellular particles, and storing the concentration in a second memory; determining a contributory hemoglobin equivalence using the concentration and a function of size of the cellular particles; removing obtained contributory hemoglobin equivalence from the apparent hemoglobin concentration to obtain a corrected hemoglobin concentration of the blood sample; and reporting the corrected hemoglobin concentration of the blood sample.

In one embodiment, the first sample mixture portion and the second sample mixture portion are prepared together by mixing one aliquot of the blood sample with a lytic reagent to lyse red blood cells therein. In another embodiment, the first sample mixture portion is prepared by mixing a first aliquot of the blood sample with a first lytic reagent to lyse red blood cells therein, and the second sample mixture portion is prepared by mixing a second aliquot of the blood sample with a second lytic reagent to lyse red blood cells therein. In a further embodiment, the first sample mixture portion is prepared by mixing a first aliquot of the blood sample with a first lytic reagent to lyse red blood cells therein, and the second sample mixture portion is prepared by mixing a second aliquot of the blood sample with a diluent for measuring platelets.

In a further embodiment, the process further comprises comparing the concentration of the cellular particles to one or more predetermined criteria, and when the concentration of the cellular particles exceeds one or more predetermined criteria, then initiating the correction process.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

Figure 5A:
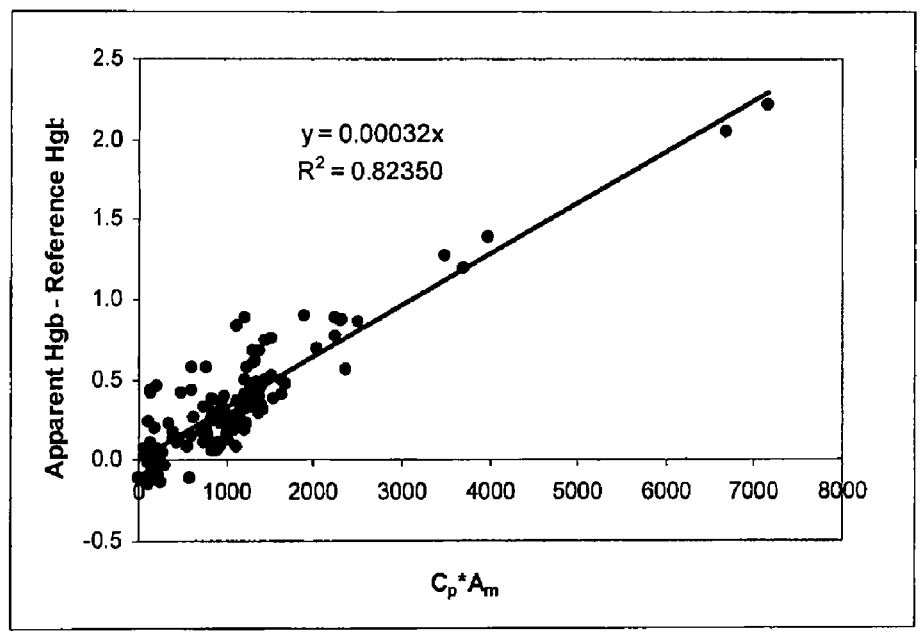
Figure 5B:
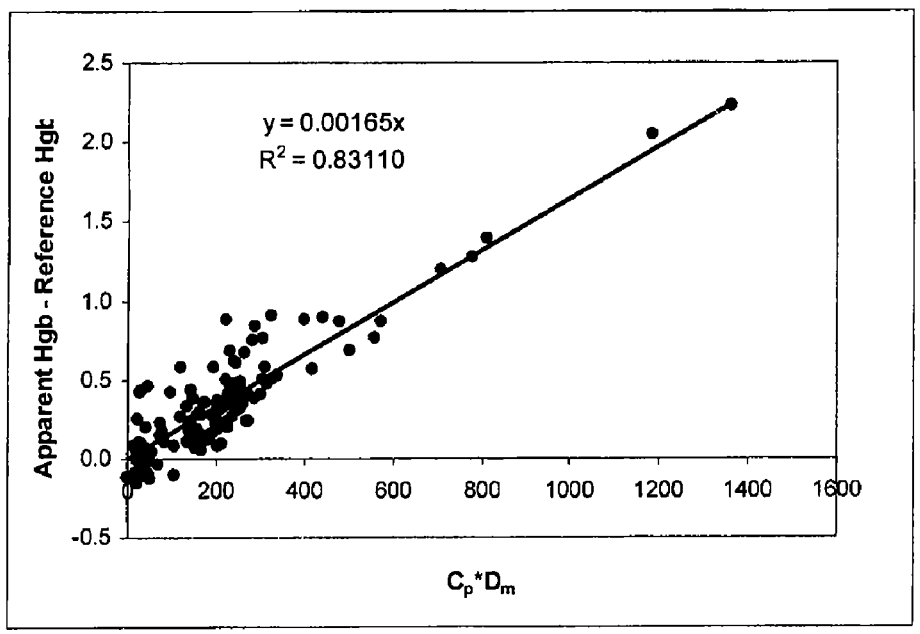

FIG. 5A shows a correlation curve of the difference between the apparent hemoglobin concentration and the reference hemoglobin concentration of blood samples and the product of the total cellular particle concentration ($C_p$) and the mean cross-section area ($A_m$) of the cellular particles. FIG. 5B shows a correlation curve of the difference between the apparent hemoglobin concentration and the reference hemoglobin concentration of blood samples and the product of the total cellular particle concentration ($C_p$) and the mean diameter ($D_m$) of the cellular particles.

Figure 6:
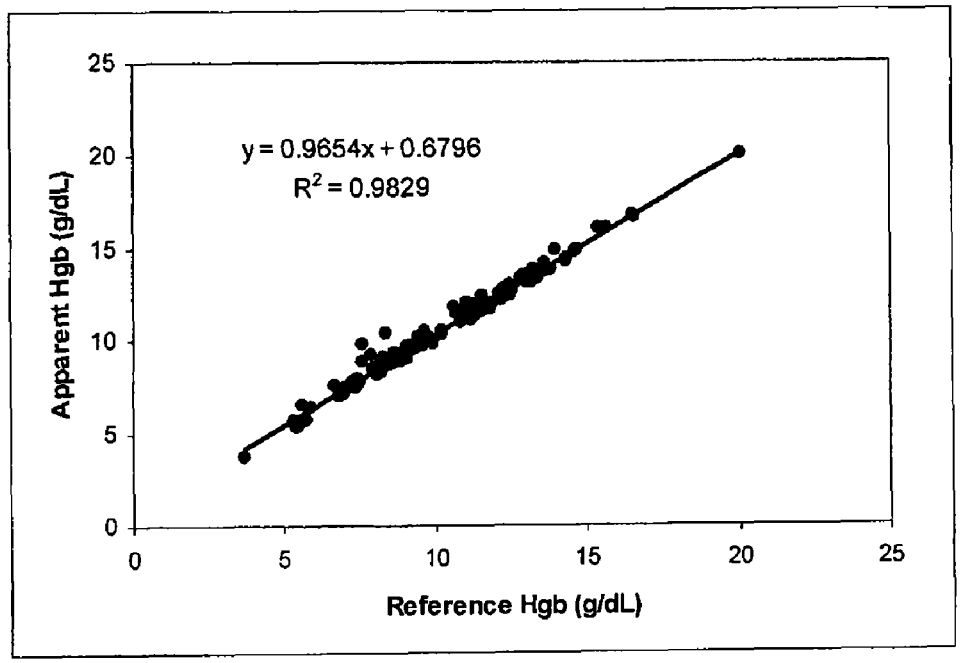

FIG. 6 shows a correlation curve of the apparent hemoglobin concentration and the reference hemoglobin concentration of 143 blood samples, measured using the experimental hematology analyzer and the reference method described in Example 1.

Figure 7:
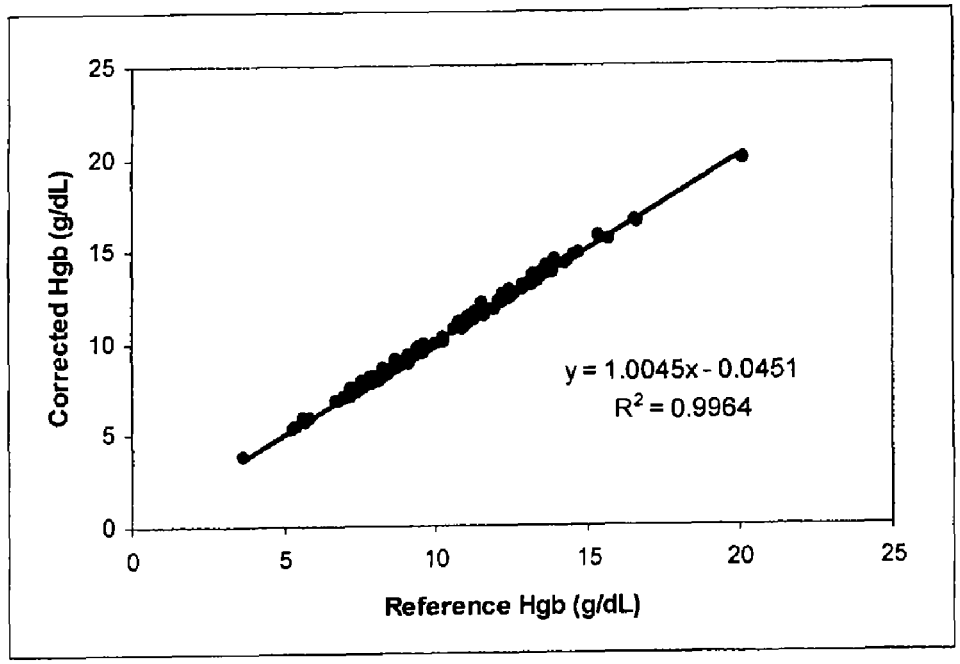

FIG. 7 shows a correlation curve of corrected hemoglobin concentration and the reference hemoglobin concentration of the same blood samples shown in FIG. 6, wherein the corrected hemoglobin concentration is obtained using a function of the total cellular particle concentration and weighted mean volume of the cellular particles in the sample mixture.

Figure 8:
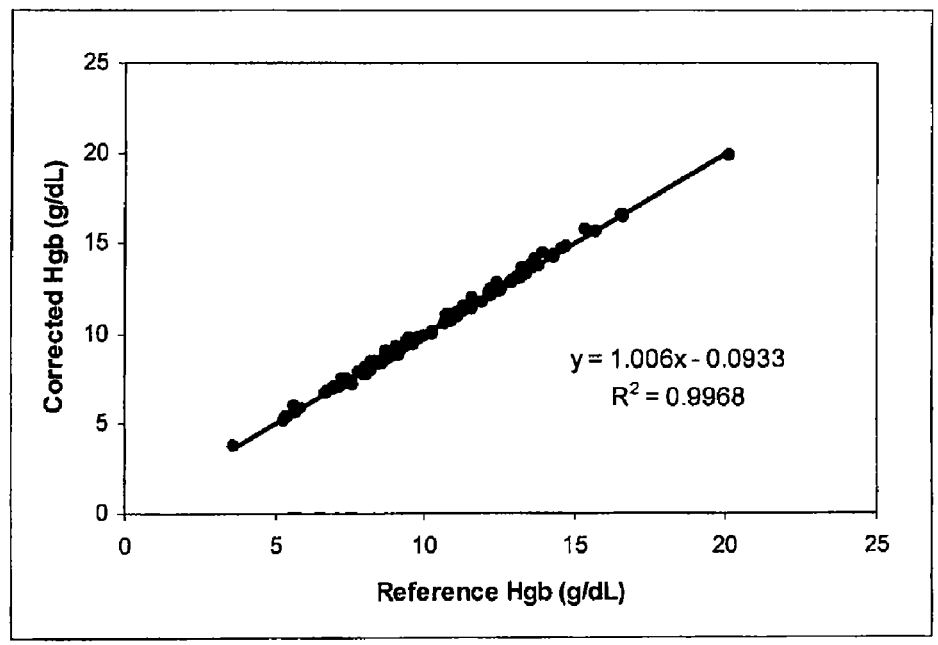

FIG. 8 shows a correlation curve of corrected hemoglobin concentration and the reference hemoglobin concentration of the same blood samples shown in FIG. 6, wherein the corrected hemoglobin concentration is obtained using a function of the total cellular particle concentration and weighted mean cross-section area of the cellular particles in the sample mixture.

Figure 9:
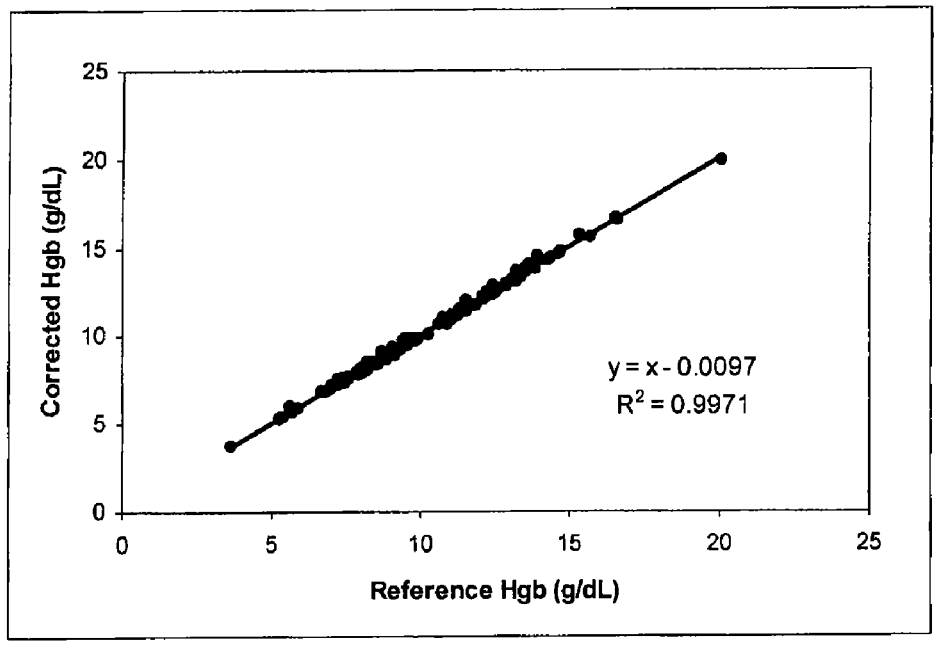

FIG. 9 shows a correlation curve of corrected hemoglobin concentration and the reference hemoglobin concentration of the same blood samples shown in FIG. 6, wherein the corrected hemoglobin concentration is obtained using a function of the total cellular particle concentration and weighted mean diameter of the cellular particles in the sample mixture.

The features and advantages of the present invention will become more apparent from the detailed description set forth below when taken in conjunction with the drawings, in which like reference characters identify corresponding elements throughout.

DETAILED DESCRIPTION

The present invention is directed towards methods of correcting particle interference to hemoglobin measurement of blood samples. This specification discloses one or more embodiments that incorporate the features of this invention. The disclosed embodiment(s) merely exemplify the invention. The scope of the invention is not limited to the disclosed embodiment(s). The invention is further defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

In one embodiment, the present invention provides a method of correction of particle interference to hemoglobin measurement of a blood sample on hematology analyzers. More specifically, the method comprises (a) mixing an aliquot of a blood sample with a lytic reagent to lyse red blood cells and forming a sample mixture; (b) measuring absorbance of the sample mixture at a predetermined wavelength of a hemoglobin chromogen formed in the sample mixture, and obtaining an apparent hemoglobin concentration of the blood sample using obtained absorbance; (c) measuring concentration and size of cellular particles remaining in the sample mixture; (d) removing contribution of the cellular particles to the apparent hemoglobin concentration using the concentration and the size of the cellular particles to obtain a corrected hemoglobin concentration of the blood sample; and (e) reporting the corrected hemoglobin concentration of the blood sample. The term "reporting" should be interpreted broadly to include such actions as: preparing a paper printout; providing an electronic record; displaying information on a monitor (or other display unit); transferring information from one instrument to another; or other equivalent functions.

The term cellular particles used herein refers to various particles remaining in a sample mixture after mixing a blood sample with a lytic reagent, which include nucleated blood cells (such as white blood cells and nucleated red blood cells), platelets, giant platelets, platelet clumps, unlysed red blood cells, and cellular debris. Among these cellular particles, white blood cells are usually most abundant. In a normal blood sample, white blood cells or leukocytes include five major subpopulations, lymphocytes, monocytes, neutrophils, eosinophils, and basophils. The latter three types of white blood cells are collectively referred to as granulocytes. In abnormal blood samples, various clinically abnormal leukocyte populations, such as blasts, immature granulocytes, metamyelocytes, myelocytes, promyelocytes, variant lymphocytes, etc., may also present. Depending on the lytic reagent and the specific reaction condition used on a hematology analyzer, the size of the white blood cell subpopulations can vary substantially. In general, when exposed to a relatively mild lytic reagent under a relatively mild reaction condition, the size of the white blood cell subpopulations can be substantially maintained in their native form. This is commonly the situation when a five-part differential analysis of the white blood cells is performed, namely differentiating white blood cells into the above mentioned five major subpopulations. However, when exposed to a stronger lytic reagent, the white blood cells are also partially lysed. Under this condition, the cellular membrane is partially damaged and cytoplasm is substantially released. This is commonly the situation when a three-part or a two-part differential analysis of the white blood cells is performed, namely differentiating white blood cells into lymphocytes, monocytes and granulocytes, or differentiating white blood cells into lymphoid cells and myeloid cells, respectively. Moreover, when exposed to a very strong lytic reagent, the white blood cells may collapse close to a single population.

Under lysing conditions, nucleated red blood cells are typically partially lysed. Their cellular membrane is damaged and the cytoplasm is released. These partially lysed cells are substantially at their nuclear volume, which is typically smaller than white blood cells.

Platelets are substantially smaller than white blood cells. In a normal blood sample, platelets are from 2 to 25 femtoliters (fL). Under lysing conditions, platelets are typically further shrunk in size. Among the cellular particles described above, platelets are among the smallest particles in the sample mixture that is used for hemoglobin measurement. However, giant platelets and platelet clumps can have a size close to white blood cells. On the other hand, in terms of abundance, giant platelets and platelet clumps are typically substantially less abundant than white blood cells in a blood sample.

With some clinical samples, the red blood cells are more difficult to lyse, for example, blood samples from sickle cell crisis patients and blood samples having high lipid contents such as cholesterol or triglyceride. Accordingly, these samples are commonly referred to as hard-to-lyse samples. With these blood samples, the sample mixture used for hemoglobin measurement often contains unlysed red blood cells as well as a substantial amount of cellular debris. The cellular debris may include unlysed cellular membrane, aggregates of cellular membrane, and other cellular components.

The term "apparent hemoglobin concentration" used herein refers to the hemoglobin concentration of a blood sample measured from a sample mixture in the presence of one or more types of the cellular particles described above. The term "corrected hemoglobin concentration of a blood sample" is the hemoglobin concentration obtained using a correction process of the present invention as described in detail hereinafter. The term "reference hemoglobin concentration" used herein refers to the hemoglobin concentration of a blood sample obtained using a reference method, such as the CLSI H15-A3 reference method. The term "correction process" used herein refers to one or more sample analysis processes which correct the contribution to hemoglobin measurement by cellular particles in the sample mixture used for hemoglobin measurement.

The term "size of cellular particles" used herein refers to the particle size expressed using volume, cross-section area, diameter, or radius of the particle. The term "cross-section area" refers to the area of the cross-section of a particle passing through the center of the particle, assuming that the particle is spherical.

In the process described above, when a blood sample is mixed with a lytic reagent, the red blood cells are completely lysed, and hemoglobin molecules are released to the sample mixture. The released hemoglobin molecules react with a ligand and form a stable chromogen. The hemoglobin chromogen is measured by spectroscopy at a predetermined wavelength in the visible region, typically between 400 nm and 680 nm. On a hematology analyzer, the sample mixture is prepared in a mixing chamber or a bath, with a dilution ratio typically from about 50:1 to about 300:1. The sample mixture is caused, typically by a vacuum force, to pass through a cuvette with a light source on one side and a detector on the opposing side. The light transmitted through the cuvette is measured at the predetermined wavelength, which is inversely proportional to the absorbance of the light by the hemoglobin chromogen, and is used to calculate hemoglobin concentration of the blood sample according to the Beer-Lambert law. As further described in detail hereinafter, cellular particles remaining in the sample mixture cause a loss of the transmitted light by scattering and absorption of the incident light. Therefore, the hemoglobin concentration obtained in this measurement is herein referred to as the apparent hemoglobin concentration, which includes a certain degree of error caused by the interference of the cellular particles to the measurement. In measuring normal and most clinical blood samples, the white blood cells are in a concentration range of $4\times10^3$ to $9\times10^3$ per microliter (μL), the error caused by the remaining white blood cells in the sample mixture is less than 0.1 gram per deciliter (g/dL), which is within the error range of hemoglobin measurement and is considered negligible. Therefore, it should be understood that in the absence of interference, the apparent hemoglobin concentration obtained on the hematology analyzer is the true hemoglobin concentration of a blood sample.

Various lytic reagents known in the art can be used for measuring hemoglobin concentration for the purpose of the present invention. In general, lytic reagents used for hemoglobin measurement comprise one or more lytic agent, typically one or more surfactant in an amount sufficient to lyse red blood cells in the sample mixture, and a ligand or a hemoglobin stabilizer in an amount sufficient to form a stable chromogen with hemoglobin. For some lytic reagents, the surfactant can also form a stable chromogen with hemoglobin for the measurement. Alternatively, the ligand is contained in a blood diluent used together with a lytic reagent.

In one embodiment, a lytic reagent can be used with a blood diluent, wherein a blood sample is diluted first with an isotonic blood diluent and then the lytic reagent is added and mixed to form the sample mixture. Suitable lytic reagents include, but are not limited to, those described in U.S. Pat. Nos. 4,346,018, 4,962,038, 5,763,280, 5,834,315, 6,573,102, and 7,235,404, which are hereby incorporated by reference in their entirety. Suitable blood diluents include, but are not limited to, those described in U.S. Pat. Nos. 4,521,518, 4,528,274, 5,935,857 and 6,706,526, which are hereby incorporated by reference in their entirety.

Alternatively, a single lytic reagent can be used to dilute the blood sample and lyse the red blood cells. Suitable lytic reagents include, but are not limited to, those described in U.S. Pat. Nos. 5,882,934 and 5,242,832, and WO/1995/024651, which are hereby incorporated by reference in their entirety.

In one embodiment, white blood cell concentration of a blood sample is also measured using the same sample mixture used for hemoglobin measurement described above. In this measurement, a portion of the sample mixture is caused, typically by a vacuum force, to pass through one or more apertures, and the white blood cells are counted by a detector, cell by cell, to obtain white blood cell concentration of the blood sample. The white blood cell concentration of a blood sample is also commonly referred to as WBC count.

In a further embodiment, in addition to measuring white blood cell concentration, size distribution of white blood cell subpopulations is also measured using the same sample mixture used for hemoglobin measurement described above. A differential analysis of the distribution of the white blood cell subpopulations is performed to differentiate the white blood cells into two subpopulations (namely, lymphoid cells and myeloid cells), three subpopulations (namely, lymphocytes, monocytes, and granulocytes), or five subpopulations (namely, lymphocytes, monocytes, neutrophils, eosinophils, and basophils).

In one embodiment, direct current (DC) impedance measurement is used for counting and measuring size distribution of white blood cells. When a particle or a blood cell, suspended in a conductive solution, passes through a focused-flow flow-cell or a non-focused flow aperture, an electrical signal, or a pulse, can be measured due to the increase of impedance. The electrical pulses are used for counting the number of white blood cells in the sample mixture of a blood sample.

On the other hand, the pulse shape, height, and width are directly related to the volume of a particle, and can be converted to the volume of the cell measured. When a sample mixture that contains two or more blood cell subpopulations having different sizes is measured, a histogram obtained from the measurement can represent size distribution of these blood cells. The detection methods and apparatus used for blood cell counting and sizing by a blood analyzer equipped with a DC impedance measurement device are generally described in U.S. Pat. Nos. 2,656,508, 3,810,011, and 5,125,737, which are hereby incorporated by reference in their entirety. Herein, the phrase "blood cell sizing" refers to the cell size or volume measurement.

Alternatively, low angle light scatter measurement can also be used for counting and sizing the blood cells. Herein, the term "low angle light scatter" refers to light scatter signals measured in a range of less than 10° from the incident light.

It has been found by the inventors that the interference of the cellular particles in the sample mixture used for hemoglobin measurement to the absorbance measurement depends on both concentration of the cellular particles and size of these particles. In other words, the contribution of the cellular particles to the apparent hemoglobin concentration is a function of both concentration and size of the cellular particles remaining in the sample mixture. This effect can be illustrated using one exemplary embodiment of hemoglobin measurement method of the present invention.

In this exemplary embodiment, hemoglobin concentration, white blood cell concentration, and a 3-part differential of white blood cell subpopulations of a blood sample are measured using the sample mixture prepared. More specifically, an aliquot of a blood sample is diluted with an isotonic diluent first in a WBC bath on a hematology analyzer as described in Example 1 and a lytic reagent is mixed with the diluted sample to form a sample mixture, with a total dilution ratio of about 250:1. The sample mixture is drawn through a set of three non-focused flow apertures and measured using DC impedance measurement to obtain a total particle count with a predetermined threshold, and to obtain a cell size distribution histogram, referred to as white blood cell distribution histogram. The sample mixture further passes a cuvette of a defined width, which has a light source on one side and a light detector on the opposing side. In other words, the sample mixture passes through a light path with a defined distance (for example, 0.5 or 1 cm). The light transmitted through the sample mixture is measured at about 540 nm, and used to calculate the apparent hemoglobin concentration (AHgb). The total particle count is used to calculate the white blood cell concentration, and the white blood cells are further differentiated into lymphocytes, monocytes, and granulocytes using the white blood cell distribution histogram (see further details in Example 1). Moreover, the distribution histogram is further used to identify other cellular particles above the detection threshold, such as nucleated red blood cells, giant platelets, platelet clumps, and cellular debris. If the other cellular particles are present, they are removed from the white blood cells to produce a corrected white blood cell concentration.

Figure 1:
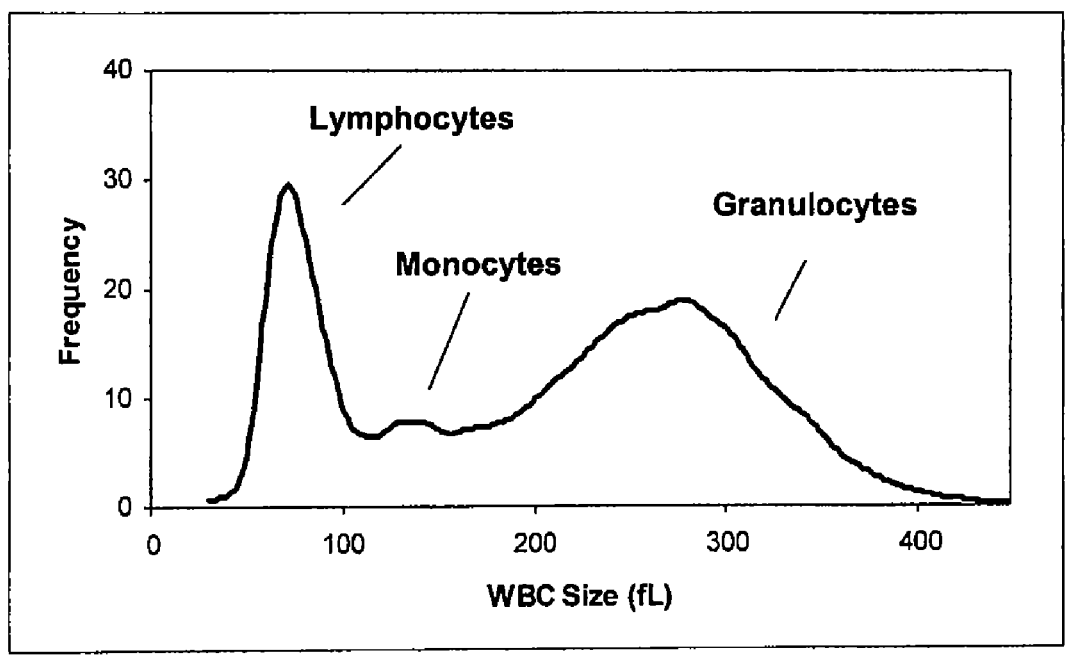
FIG. 1 shows a white blood cell distribution histogram of a normal blood sample obtained on the hematology analyzer as described in Example 1.

FIG. 1 shows a white blood cell distribution histogram of a normal blood sample obtained on the hematology analyzer described in Example 1. As shown, in this sample mixture lymphocytes have a size from about 30 fL to about 110 fL, monocytes have a size from about 110 fL to about 170 fL, and granulocytes have a size from about 170 fL to about 450 fL. As can be appreciated from the histogram, in the sample mixture different white blood cell subpopulations can be substantially different in size.

As described in Example 1, 143 whole blood samples collected from four hospitals were analyzed on experimental hematology analyzers. About 75% of these blood samples had a high white blood cell concentration, from $11 \times 10^3/\mu L$ to $260 \times 10^3/\mu L$. The hemoglobin concentration of these same blood samples was also measured using the CLSI reference method, with which the whole blood samples were filtered through a 0.2 μm filter to remove white blood cells prior to a manual measurement of the absorbance on a spectrophotometer.

Figure 2:
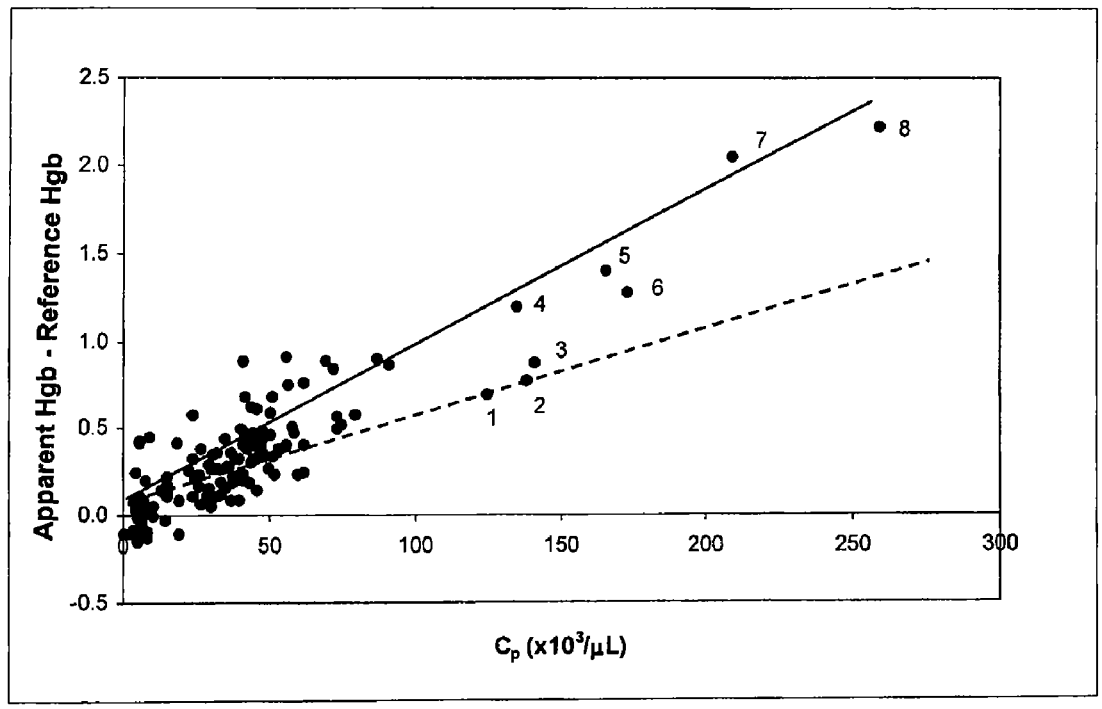
FIG. 2 illustrates a dependency of the difference between the apparent hemoglobin concentration and the reference hemoglobin concentration of blood samples on the concentration and the size of white blood cells.
Figure 3A:
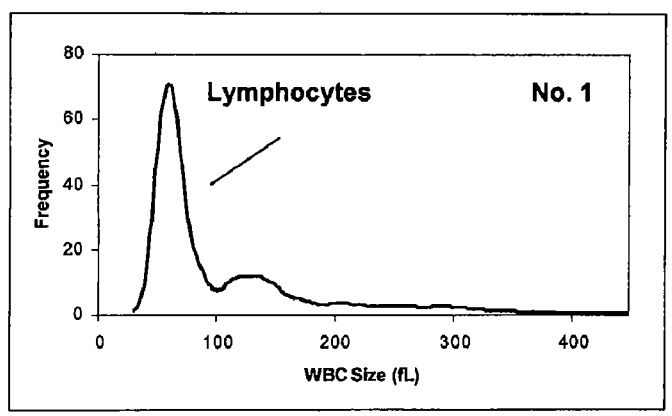
FIGS. 3A through 3D illustrate white blood cell size distribution histograms of four clinical abnormal blood samples, all having an extremely high white blood cell concentration, but having different subpopulation concentrations.
Figure 3B:
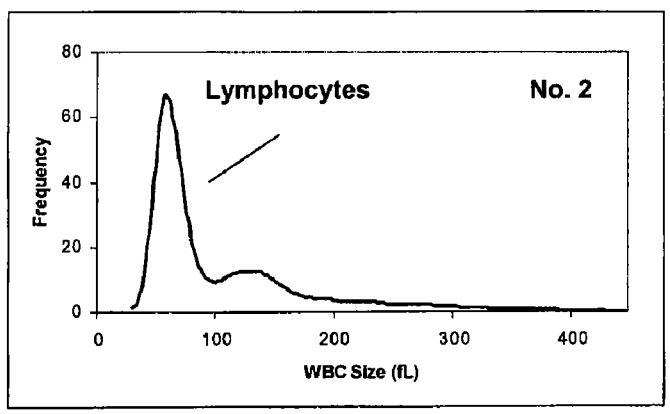
Figure 3C:
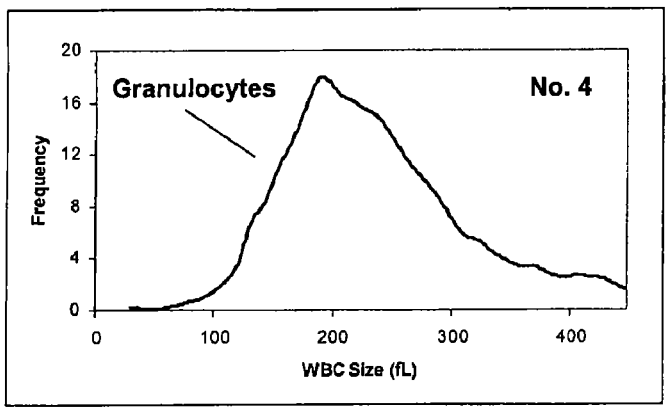
Figure 3D:
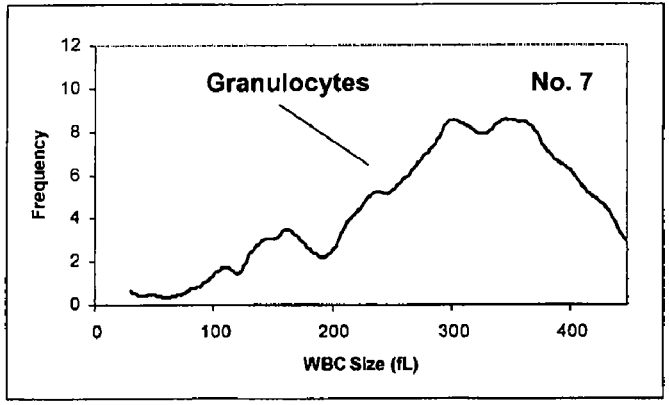

FIG. 2 illustrates the dependency of the obtained apparent hemoglobin concentration of these blood samples on the concentration and size of the cellular particles remaining in the sample mixture. In FIG. 2, in the graph the X-axis is the total particle concentration ($C_p$) without removing other cellular particles from the white blood cells (also referred to as raw WBC); and the Y-axis is the difference between the apparent hemoglobin concentration (Apparent Hgb) and the hemoglobin concentration obtained using the reference method, which is referred to as reference hemoglobin concentration (Reference Hgb). The difference between the apparent hemoglobin concentration and the reference hemoglobin concentration is mainly attributed to the interference of the cellular particles, particularly white blood cells in these high WBC samples. It is noted that the small difference of about ±0.2 g/dL observed near the origin of the graph is within the error range of the method on the hematology analyzer, which typically has an accuracy of ±0.2 g/dL; moreover the error range of the manual reference method is higher than that of an automated hematology analyzer. In the table below the graph, the total particle concentration (raw WBC) and percentages of subpopulations of eight blood samples having an extremely high white blood cell concentration, above $100 \times 10^3/\mu L$, are provided. The sample number for each of these eight blood samples is also shown next to the corresponding data point on the graph.

As shown in the graph, the difference between the apparent hemoglobin concentration and the reference hemoglobin concentration increases with the total particle concentration. Moreover, dependency of the extent of interference on the particle size can be clearly appreciated using the eight blood samples shown in the table. More specifically, blood sample Nos. 1, 2 and 3 have an abnormally high lymphocyte percentage, 64.1%, 61.0%, and 61.8, respectively, and an abnormally low granulocyte percentage, 14.4%, 14.7%, and 13.2% respectively. Among these three samples, the white blood cell concentration increases from blood sample No. 1 to No. 3, and hence, the difference (Apparent Hgb−Reference Hgb) increases in the same direction.

On the other hand, blood sample No. 4 has a similar white blood cell concentration to that of blood sample No. 2, i.e., $135.5 \times 10^3/\mu L$ for the former and $138.6 \times 10^3/\mu L$ for the latter. However, blood sample No. 4 has an abnormally high granulocyte percentage of 96.1% and an abnormally low lymphocyte percentage of 0.2%. As shown in the graph, the difference (Apparent Hgb−Reference Hgb) is substantially different between these two samples, which is significantly higher in blood sample No. 4.

Similar to blood sample No. 4, blood sample Nos. 7 and 8 also have an abnormally high granulocyte percentage, 86.2% and 83.1%, respectively, and an abnormally low lymphocyte percentage, 0.2% and 0.5%, respectively.

As shown in the graph of FIG. 2, blood sample Nos. 4, 7, and 8 fall on the solid line, which reflects a linear correlation between the hemoglobin difference (Apparent Hgb−Reference Hgb) and the total particle concentration. On the other hand, blood sample Nos. 1, 2, and 3 fall on the broken line, which also reflects a linear correlation between the difference (Apparent Hgb−Reference Hgb) and the total particle concentration, but with a significantly smaller slope than that of the solid line.

As can be further appreciated, blood sample Nos. 5 and 6 have an abnormally high monocyte percentage and reduced granulocyte percentage. It is noted that the data points from these two samples fall between the solid line and the broken line.

FIGS. 3A through 3D show the white blood cell histograms of blood sample Nos. 1, 2, 4, and 7, respectively. As shown, blood sample Nos. 4 and 7 contain primarily substantially larger particles than those in blood sample Nos. 1 and 2.

The experimental results shown in FIG. 2 clearly indicate that the interference of the cellular particles to hemoglobin measurement, or their contribution to the apparent hemoglobin concentration, increases with the size of the cellular particles.

This size dependency is further illustrated using an analog model. As described in Example 2, two different types of cellular analogs having different sizes are used to assess the size contribution to the interference of hemoglobin measurement. The cellular analogs are the lymphocyte and granulocyte analogs used for making reference control for 3-part differential analysis on hematology analyzers described in Examples 1 and 2. In this experiment, two sets of simulated high white blood cell samples are prepared. In the first set, 9 identical aliquots of a normal whole blood sample are dispensed into test tubes, then a predetermined amount of lymphocyte analog suspension is added, in an increasing order, to the test tubes to create simulated high white blood cell samples with only the simulated lymphocytes. Similarly, in the second set, 9 identical aliquots of a normal whole blood sample are dispensed into test tubes, then a predetermined amount of granulocyte analog suspension is added, in an increasing order, to the test tubes to create simulated high white blood cell samples with only the simulated granulocytes. It is noted that as the amount of the cellular analogs increases, the concentration of hemoglobin in the test tube decreases because of dilution caused by the addition of the analogs suspended in a liquid medium. These test samples are then analyzed on a hematology analyzer as described in Example 2, in the same manner of analyzing a blood sample. The correlation of the obtained apparent hemoglobin concentration and white blood cell concentration is shown in FIG. 4.

Figure 4:
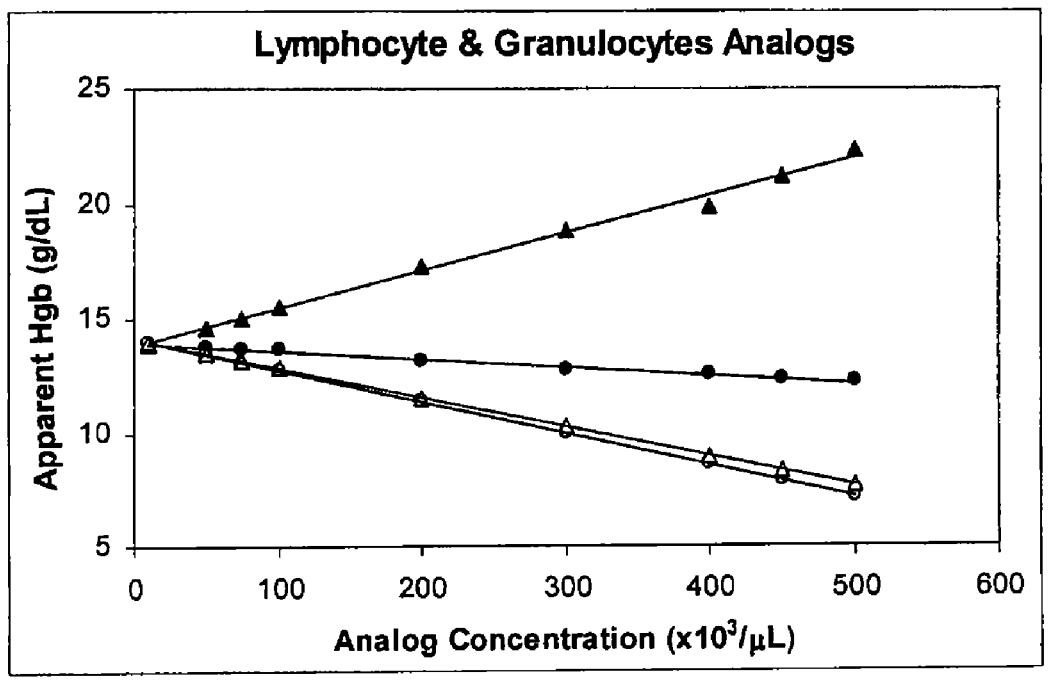
FIG. 4 shows correlation curves of apparent hemoglobin concentration of a blood sample and white blood cell concentration with addition of two different sizes of cellular analogs.

In FIG. 4, the X-axis is the analog concentration and the Y-axis is the apparent hemoglobin concentration. The data points expressed by the solid symbols (along the top two lines) are the apparent hemoglobin concentration obtained from the two sets of test samples. The data points expressed by the hollow symbols are the theoretical hemoglobin concentration calculated according to the degree of dilution caused by addition of the analog suspension.

As shown in FIG. 4, after taking account for dilution, the hemoglobin concentration of these two sets of test samples should linearly decrease in the order shown in the lower two lines. However, because of the interference caused by the cellular analogs, the obtained apparent hemoglobin concentrations are substantially higher. As shown, the apparent hemoglobin concentration increases with the increase of the analog concentration. More importantly, the apparent hemoglobin concentrations are substantially higher in the test samples containing the granulocyte analogs than those containing the lymphocyte analogs.

As can be appreciated from the histograms illustrated in FIGS. 1 and 3A-3D, each blood sample may have a different particle size distribution, particularly with various clinically abnormal blood samples. However, despite the complexity and significant variations among samples, the present inventors have discovered unexpectedly the contribution of the cellular particles, particularly the nucleated blood cells, to the apparent hemoglobin concentration can be effectively corrected using a function of the concentration and the size of the cellular particles in the sample mixture used for hemoglobin measurement.

In one embodiment, the contribution of the cellular particles to the apparent hemoglobin concentration is defined as contributory hemoglobin equivalence, which is a function of concentration and size of the cellular particles in the sample mixture used for hemoglobin measurement. More specifically, contributory hemoglobin equivalence can be expressed mathematically as a product function of concentration ($C_p$) and a size factor ($S_f$) of the cellular particles in the sample mixture and a conversion factor.

In one embodiment, the contribution of the cellular particles to the apparent hemoglobin concentration can be removed by using equation 1 below:

$$Hgb = AHgb - \beta * C_p * S_f \qquad (1)$$

wherein, Hgb is the corrected hemoglobin concentration of a blood sample; AHgb is the apparent hemoglobin concentration as defined above; β is a conversion factor, which can be determined experimentally as described further hereinafter; $C_p$ is the total cellular particle concentration in the sample mixture, as measured by the particle measurement device. It should be understood that the cellular particles being measured are above the detection threshold of the particle measurement device, which do not include the smaller particles that fall below the threshold. As can be understood, in the absence of an appreciable amount of other cellular particles, $C_p$ is substantially the same as the white blood cell concentration of the blood sample. $S_f$ is the size factor, which is a function of size of all cellular particles being measured by the particle measurement device used on the hematology analyzer.

As can be appreciated, the size of cellular particles can be expressed by different parameters, such as by volume, cross-section area, or diameter of the particles. Using a DC impedance measurement, the electrical pulse shape, height and width generated by a cellular particle are directly related to the volume of the particle, and can be converted to the volume of the particle. The measured volume of cellular particles is traditionally reported in femtoliter as shown in FIG. 1. As can be understood, the white blood cells in the sample mixture may not be perfectly spherical. However, for the purpose of the present invention the cellular particles can be approximated as spherical particles. Therefore, the relationship among volume, cross-section area, diameter and radius of a spherical particle can be used when the size of the cellular particles is expressed using different parameters.

In one embodiment, $S_f$ is defined by the mean volume ($V_m$) of the cellular particles in the sample mixture. Therefore, equation 1 above can be expressed as follows:

$$Hgb = AHgb - \beta_v * C_p * V_m \qquad (2)$$

In equation 2, $\beta_v$ is a conversion factor which can be determined experimentally as described below; and $C_p$ is the total cellular particle concentration in the sample mixture as defined above. The mean volume ($V_m$) includes weighted mean volume, geometric mean volume, mode volume, median volume, or other suitable mean of the volume of the cellular particles.

Preferably, $V_m$ is a weighted mean volume of the cellular particles in the sample mixture, which can be obtained according the following equation:

$$V_m = \frac{\sum_{i=1}^{N} f_i \cdot v_i}{\sum_{i=1}^{N} f_i} \qquad (3)$$

wherein i is the index of a channel on the white blood cell distribution histogram; $v_i$ is the volume of cellular particles in the ith channel; $f_i$ is the frequency of pulses in the ith channel, which represents the number of particles in the ith channel; and N is the total number of channels on the white blood cell distribution histogram.

In the measurement of size distribution of the cellular particles, such as the differential analysis of white blood cells described above, a channelizer with a predetermined resolution, typically 256 channels, is used. The amplitude of an electrical pulse generated by a particle corresponds to the size of the particle. When the instrument is calibrated with reference particles of a known volume, then each channel corresponds to a known volume. Therefore, electrical pulses during the measurement of the sample mixture are collected in different channels depending on the size of the particles. This can be appreciated from the measurement of white blood cells as shown in FIG. 1, where 256 channels are used to measure white blood cells having sizes ranging from 30 fL to 450 fL.

As can be understood, using equation 3, above, the obtained weighted mean volume of the cellular particles takes account for contributions from all particles measured in the sample mixture.

Alternatively, $V_m$ can also be expressed by geometric mean volume, mode volume, median volume, or other suitable mean of the volume of the cellular particles. These parameters are different representations of the mean volume of the cellular particles and can be determined from the white blood cell distribution histogram of a blood sample.

The conversion factor $\beta_v$ can be determined experimentally. Equation 2 above can be rearranged as shown below:

$$\beta_v = (AHgb - Hgb)/(C_p * V_m) \qquad (4)$$

As shown in equation 4, AHgb, $V_m$, and $C_p$ can be determined on the hematology analyzer as described above, and Hgb can be determined using the reference method. Mathematically, $\beta_v$ is the slope of a correlation curve of AHgb–Hgb versus $C_p*V_m$. Therefore, $\beta_v$ can be derived from measurement of multiple blood samples including those having high white blood cell concentrations.

It is noted that the cellular particle concentration $C_p$ can also be expressed in a unit equivalent to the concentration of the particles in a blood sample. Since on a hematology analyzer white blood cell concentration is always reported as the concentration of the cells in a whole blood, after considering the dilution made in the measurement, the total cellular particle concentration in the sample mixture can be expressed in the same manner. As long as β is obtained and used for correction in consistent with the unit of $C_p$, the relationship between the particle concentration and its effect on hemoglobin remains the same.

In another embodiment, $S_f$ is defined by mean cross-section area $(A_m)$ of the cellular particles in the sample mixture. Therefore, equation 1 above can be expressed by equation 5 below:

$$Hgb = AHgb - \beta_A * C_p * A_m \qquad (5)$$

In equation 5, $\beta_A$ is the conversion factor which can be determined experimentally as described below; and $C_p$ is the total cellular particle concentration in the sample mixture as defined above. The mean cross section are $(A_m)$ includes weighted mean cross-section area, geometric mean cross-section area, mode cross-section area, median cross-section area, or other suitable mean of the cross-section area of the cellular particles.

Preferably, $A_m$ is a weighted mean cross-section area of the cellular particles in the sample mixture, which can be obtained according the following equation:

$$A_m = \frac{\sum_{i=1}^{N} f_i \cdot v_i^{2/3}}{\sum_{i=1}^{N} f_i} \qquad (6)$$

wherein i is the index of a channel on the white blood cell distribution histogram; $v_i$ is the volume of cellular particles in the ith channel; $f_i$ is the frequency of pulses in the ith channel, which represents the number of particles in the ith channel; and N is the total number of channels on the white blood cell distribution histogram.

As can be understood, the cross-section area (A) and the volume (V) of a spherical particle have the relationship that A is proportional to $V^{2/3}$. Therefore, in equation 6, $V_i^{2/3}$ corresponds to the cross-section area of each particle in the ith channel.

Alternatively, $A_m$ can also be expressed by geometric mean cross-section area, mode cross-section area, median cross-section area, or other suitable mean of the cross-section area of the cellular particles. These parameters are different representations of the mean cross-section area of the cellular particles, and can be derived from the corresponding mean volume described above, based on the relationship of $A_m = \text{constant} * V_m^{2/3}$.

Similar to $\beta_v$, the conversion factor $\beta_A$ can be determined experimentally according to equation 7.

$$\beta_A = (AHgb - Hgb)/(C_p * A_m) \qquad (7)$$

Similarly, AHgb, $A_m$ and $C_p$ can be determined on the hematology analyzer as described above, and Hgb can be determined using the reference method. Mathematically, $\beta_A$ is the slope of a correlation curve of AHgb–Hgb versus $C_p*A_m$. Therefore, $\beta_A$ can be derived from measurement of multiple blood samples including those having high white blood cell concentrations.

In a further embodiment, $S_f$ is defined by mean diameter $(D_m)$ of the cellular particles in the sample mixture. Therefore, equation 1 above can be expressed by equation 8 below:

$$Hgb = AHgb - \beta_D * C_p * D_m \qquad (8)$$

In equation 8, $\beta_D$ is the conversion factor which can be determined experimentally as described below; and $C_p$ is the total cellular particle concentration in the sample mixture as defined above. The mean diameter $(D_m)$ includes weighted mean diameter, geometric mean diameter, mode diameter, or median diameter, or other suitable mean of the diameter of the cellular particles.

Preferably, $D_m$ is a weighted mean diameter of the cellular particles in the sample mixture, which can be obtained according the following equation:

$$D_m = \frac{\sum_{i=1}^{N} f_i \cdot v_i^{1/3}}{\sum_{i=1}^{N} f_i} \qquad (9)$$

wherein i is the index of a channel on the white blood cell distribution histogram; $v_i$ is the volume of cellular particles in the ith channel; $f_i$ is the frequency of pulses in the ith channel, which represents the number of particles in the ith channel; and N is the total number of channels on the white blood cell distribution histogram.

As can be understood, the diameter (D) and the volume (V) of a spherical particle have the relationship that D is proportional to $V^{1/3}$. Therefore, in equation 9, $V_i^{1/3}$ corresponds to the diameter of each particle in the ith channel.

Alternatively, $D_m$ can also be expressed by geometric mean diameter, mode diameter, or median diameter, or other suitable diameter of the cellular particles. These parameters are different representations of the mean diameter of the cellular particles, and can be derived from the corresponding mean volume described above, based on the relationship of $D_m = \text{constant} * V_m^{1/3}$.

Similar to $\beta_v$, the conversion factor $\beta_D$ can be determined experimentally according to equation 10.

$$\beta_D = (AHgb - Hgb)/(C_p * D_m) \qquad (10)$$

Similarly, AHgb, $D_m$ and $C_p$ can be determined on the hematology analyzer as described above, and Hgb can be determined using the reference method. Mathematically, $\beta_D$ is the slope of a correlation curve of AHgb–Hgb versus $C_p*D_m$. Therefore, $\beta_D$ can be derived from measurement of multiple blood samples including those having high white blood cell concentrations.

FIG. 5A shows the correlation curve of AHgb–Hgb versus $C_p*A_m$, and FIG. 5B shows the correlation curve of AHgb–Hgb versus $C_p*D_m$, respectively. FIGS. 5A and 5B are produced by using those 143 blood samples analyzed on the hematology analyzer as described in Example 1. In both figures, the Y-axis is the difference between the apparent hemoglobin concentration and the reference hemoglobin concentration, which corresponds to (AHgb–Hgb) in equations 7 and 10. In FIG. 5A, X-axis is the product of the total cellular particle concentration in the sample mixture $(C_p)$ and the mean cross-section area $(A_m)$ obtained using equation 6, and in FIG. 5B, X-axis is the product of the total cellular particle concentration in the sample mixture $(C_p)$ and the mean diameter ($D_m$) obtained using equation 9. Here, $A_m$ and $D_m$ are weighted cross-section area and weighted diameter, respectively, obtained by post analysis of the list mode data received from the channelizer. The solid line in both figures is the correlation curve obtained from a linear regression analysis. From the correlation curves the conversion factors $\beta_A$ and $\beta_D$ can be derived. In this case, $\beta_A$ is the slope of 0.00032 in FIG. 5A and $\beta_D$ is the slope of 0.00165 in FIG. 5B, respectively.

Using the embodiment defined by equation 5 as an example, once $\beta_A$ is determined, the corrected hemoglobin concentration (Hgb) of each blood sample can be obtained using the parameters, more specifically AHgb, $A_m$, $C_p$, obtained on hematology analyzer according to equation 5.

Similarly, for embodiments defined by equations 2 and 8, once $\beta_V$ and $\beta_D$ are determined, the corrected hemoglobin concentration (Hgb) of each blood sample can be obtained using the parameters obtained on the hematology analyzer according to equations 2 and 8, respectively.

Furthermore, as can be appreciated from FIG. 5A, the difference between the apparent hemoglobin concentration and the reference hemoglobin concentration has a substantially better correlation with $C_p*A_m$ than that with $C_p$ shown in FIG. 2. In FIG. 5A, the scattered data points are brought along the linear regression line. A similar effect is also observed in FIG. 5B. As can be appreciated, the product function of the total cellular particle concentration and the mean cross-section area, $C_p*A_m$, reflects the total cross-section area of the cellular particles. Similarly, the product function of the total cellular particle concentration and the mean diameter, $C_p*D_m$, reflects the total diameter of the cellular particles; and the product function of the total cellular particle concentration and the mean volume, $C_p*V_m$, reflects the total volume of the cellular particles. The results shown indicate these product functions effectively reflect or simulate the effect of interference caused by cellular particles.

Without being bound to any theory, the correction process described above may be better understood based on the light extinction property of particles. It is known that in a particle suspension exposed to an incident light, the particles scatter and absorb the light, and both cause loss of the light transmitted through the suspension. As a result, the actual or apparent transmittance ($T_A$), i.e., the light transmitted through the cuvette containing the sample mixture, can be expressed as follows:

$$T_A = T_T(1-x) \tag{11}$$

where, $T_A$ is the apparent transmittance; $T_T$ is the true or theoretical transmittance of the sample mixture if the particles are not present; and x corresponds to the loss of transmitted light due to scattering and absorbance of the particles.

Then, the apparent hemoglobin concentration (AHgb) of a blood sample obtained from measuring the sample mixture can be expressed by equation 12:

$$AHgb = \kappa \cdot \ln\left(\frac{T_0}{T_A}\right) = \kappa \cdot \ln\left(\frac{T_0}{T_T} \cdot \frac{1}{1-x}\right) \approx \kappa \cdot \ln\left(\frac{T_0}{T_T}\right) + \kappa \cdot x \tag{12}$$

where $T_0$ is the transmittance measured from a blank; and $\kappa$ is a constant.

In equation 12, an approximation $\ln(1/(1-x)) \approx x$ can be applied, providing that $x \ll 1$. Recognize that $\kappa \ln(T_0/T_T)$ is the true hemoglobin concentration (Hgb) of the blood sample in the absence of interference of the particles, equation (12) can be expressed as follows:

$$AHgb - Hgb = \kappa x \tag{13}$$

It is known that the light extinction cross-section area ($\sigma_e$) is a function of the radius of the particle and light extinction efficiency factor of the particle, as defined by equation 14:

$$\sigma_e = Q_e * \pi * r^2 \tag{14}$$

where r is the radius of the particle; and $Q_e$ is the light extinction efficiency factor of the particle, which is a function of the reflective index and size of the particle.

The total light extinction cross-section area ($\sigma_{e/total}$) of all cellular particles measured may be assumed proportional to $\sigma_e$, and may be approximated by equation 15 below:

$$\sigma_{e/total} \propto \sum_{i=1}^{N}(Q_{ei} * \pi * r_i^2) \tag{15}$$
$$\approx Q_{av} * C_p * (\pi R_m^2)$$

where, $Q_{av}$ corresponds to average light extinction efficiency factor of the cellular particles measured; N is the total number of cellular particles measured in the sample mixture, which can be expressed by concentration; $C_p$ is the total concentration of the cellular particles; and $R_m$ is the mean radius of the cellular particles.

Assume the light loss caused by the cellular particles is related to the light extinction cross-section area ($\sigma_e$) of these particles, then equation 15 can be inserted into equation 13 as follows:

$$AHgb - Hgb = k*Q_{av}*C_p*(\pi R_m^2) \tag{16}$$

As can be appreciated, equation 16 correlates with the contributory hemoglobin equivalence defined in equation 5 discussed above, where $\pi R_m^2$ directly correlates to the mean cross-section area $A_m$ in equation 5.

Moreover, if equation 16 is modified as follows:

$$Hgb = AHgb - k_1*Q_{av}*C_p*(\pi R_m^3) \tag{17}$$

or, $$Hgb = AHgb - k_2*Q_{av}*C_p*(\pi R_m) \tag{18}$$

it is apparent that equation 17 correlates with equation 2, where $\pi R_m^3$ directly correlates to mean volume $V_m$; and equation 18 correlates with equation 8, where $\pi R_m$ directly correlates to mean diameter $D_m$. Here, $k_1$ and $k_2$ are constants.

As can be further appreciated, if equation 16 is modified as shown in equation 19 below, $$Hgb = AHgb - k_3^* Q_{av}^* C_p^* (\pi^* R_m^0) \tag{19}$$
$$= AHgb - k_3^* Q_{av}^* C_p^*$$

then the contributory hemoglobin equivalence reduces to a function of the total concentration of the cellular particles and the average light extinction efficiency factor of the cellular particles. Here, $k_3$ is a constant.

A correction using equation 19 can be recognized as a simplified approach, where the contribution of particle size is only reflected by the light extinction efficiency factor, without further representation by the size factor (such as $V_m$, $A_m$, or $D_m$). This simplified approach is suitable for the situation where the cellular particles are similar in size. This is often found when a strong lytic reagent is used because the white blood cells can be substantially shrunk into a single population. Such a situation can be appreciated from the results shown in FIG. 4. As discussed in Example 2, cellular analogs are used together with a whole blood sample for simulating the effect of high concentration particles having a specific size. The blood sample contains $9.73 \times 10^3/\mu L$ white blood cells, and the contribution of white blood cells to hemoglobin measurement from the blood sample itself can be neglected. For each analog, lymphocyte analog or granulocyte analog, the particle size and its size distribution (substantially a Gaussian distribution) are known. When concentration of the analog increases, the apparent hemoglobin concentration increases linearly, without further contribution from size variation.

Equation 19 can be further simplified and rearranged as follows:

$$Hgb = AHgb - \gamma * C_p* \qquad (20)$$

$$\gamma = (AHgb - Hgb)/C_p \qquad (21)$$

where $\gamma = k_3 * Q_{av}$, which can be obtained experimentally using the parameters obtained from the hematology analyzer and the reference hemoglobin concentration, as discussed above.

It is important to understand that $Q_{av}$ is a function of the reflective index and size of the particles. This is clearly shown in FIG. 4, where the slope of apparent hemoglobin concentration from the samples containing granulocyte analogs is substantially higher than the corresponding slope from the samples containing lymphocyte analogs.

In a further embodiment, different size factor $S_f$ can be used in correction of contribution of different subpopulations of the cellular particles to the hemoglobin measurement. As described above, in simulating size contribution of the cellular particles, the particles are assumed to be spherical as an approximation, although they are not ideal sphere particles. As can be appreciated, different subpopulations of the cellular particles may have different deviations from a sphere and may be better simulated by one size factor than another. Therefore, equation 1 may be expressed using different size factors for different subpopulations as shown below:

$$Hgb = AHgb - C_p*[LY\%(\beta_1*S_{f1}) + MO\%(\beta_2*S_{f2}) + GR\% \\ (\beta_3*S_{f3}) + J\%(\beta_j*S_{f4})] \qquad (22)$$

where $C_p$ is the total cellular particle concentration in the sample mixture as defined above; LY %, MO % and GR % are percentage of lymphocytes, monocytes, and granulocytes, respectively; J % is the percentage of the cellular particles other than those three white blood cell subpopulations, for example, nucleated red blood cells. It should be understood that J can be more than one population, and each has its own conversion factor $\beta_j$. $S_{f1}$, $S_{f2}$, $S_{f3}$ and $S_{f4}$ are the size factor for each corresponding subpopulation, respectively. $\beta_1$, $\beta_2$, $\beta_3$, and $\beta_j$ are the conversion factors for each corresponding subpopulation, respectively. It is noted that $C_p*LY\%$, $C_p*MO\%$, and $C_p*GR\%$ correspond to the concentration of lymphocytes, monocytes and granulocytes, respectively.

As discussed above, $C_p$ can be determined by the hematology analyzer; and LY %, MO %, GR % and J % can be determined by differential analysis of white blood cells as shown in FIGS. 1 and 2. $\beta_1$, $\beta_2$, $\beta_3$, and $\beta_j$ can be determined experimentally using the method described above and using blood samples having predominantly one subpopulation, such as sample Nos. 1, 2, 4 and 7 shown in FIG. 2, using samples with addition of a specific subpopulation harvested from a whole blood, or using samples with addition of a suitable analog.

In this embodiment, $S_{f1}$, $S_{f2}$, $S_{f3}$ and $S_{f4}$ may be different. For example, $S_{f1}$ may be defined by mean volume, $S_{f2}$ may be defined by mean cross-section area and $S_{f3}$ may be defined by mean diameter of the corresponding population, respectively. Therefore, each subpopulation may be better simulated using a specific size factor.

Moreover, as can be appreciated within each subpopulation the particle size is more similar or more uniform than it is across all subpopulations. If the simplified approach expressed by equation 20 is applied here, then equation 22 is reduced to equation 23:

$$Hgb = AHgb - C_p*(\gamma_1*LY\% + \gamma_2*MO\% + \gamma_3*GR\% + \\ \gamma_j*J\%) \qquad (23)$$

where $\gamma_1$, $\gamma_2$, $\gamma_3$, and $\gamma_j$ are conversion factors for each corresponding population, respectively. As can be understood from equation 20, each of $\gamma_1$, $\gamma_2$, $\gamma_3$, and $\gamma_j$ is a function of the reflective index and size of its corresponding subpopulation. As discussed above, LY %, MO %, GR % and J % can be determined by differential analysis of white blood cells. $\gamma_1$, $\gamma_2$, $\gamma_3$, and $\gamma_j$ can be determined experimentally using the method described above and using blood samples having predominantly one subpopulation, using samples with addition of a specific subpopulation harvested from a whole blood, or using samples with addition of a suitable analog.

It is further noted that in the embodiments defined by equations 22 and 23, the contributory hemoglobin equivalence defined in equation 1 is further expressed by subpopulation contributory hemoglobin equivalence of each subpopulation, which is a function of concentration and a size factor of the subpopulation. Moreover, removing contribution of the cellular particles is accomplished by subtracting the subpopulation contributory hemoglobin equivalence of each subpopulation from the apparent hemoglobin concentration.

In equations 22 and 23, a measurement of the cellular particles enabling differentiation of the white blood cells into three subpopulations (3-part differential analysis) is used as an example. However, it should be understood that the method of the present invention illustrated by equations 22 and 23 is not limited to 3-part differential analysis. As can be readily understood, in a situation of 2-part differential, in equations 22 and 23 the subpopulations will be lymphoid cell % and myeloid cell %, and $\beta$, $\gamma$, and $S_f$ will be the conversion factors and size factor of these two populations respectively. As can be further understood, when a very strong lytic reagent is used and the white blood cells collapse close to one population, equation 23 may be reduced to equation 20.

As discussed above, the interference to hemoglobin measurement only occurs when the sample mixture contains a substantially high concentration of cellular particles. Therefore, in a further embodiment, the method of the present invention further comprise a step of comparing the obtained cellular particle concentration to a predetermined criterion, and only when the cellular particle concentration exceeds a predetermined criterion, then initiating the correction process described above.

The predetermined criterion can be different on different hematology analyzers, depending on the lytic reagent and the reaction condition used in preparing the sample mixture for hemoglobin measurement. In general, the stronger the lytic reagent is and the smaller the cellular particles are, the higher the tolerable cellular particle concentration is before it is needed to initiate the correction process. The predetermined criterion can be determined empirically on each type of hematology analyzer, using the reagents under the reaction condition intended for hemoglobin measurement. Depending on the instrument's accuracy requirement, typically an error of about 0.1 to 0.2 g/dL, caused by the interference of the particles, can be used in determining the criterion for initiating the correction process. In one embodiment, the predetermined criterion is defined as the cellular particle concentration being equal to $11 \times 10^3/\mu L$ in measuring white blood cells and other cellular particles having a similar size. With this criterion, when the cellular particle concentration of a blood sample exceeds $11 \times 10^3/\mu L$, correction using the method described is performed.

Example 1 illustrates the effectiveness of using equations 2, 5 and 8 to correct interference of cellular particles by removing the contribution of the cellular particles to the apparent hemoglobin concentration. 143 blood samples were analyzed on a hematology analyzer as described in Example 1, and the same blood samples were also analyzed using the CLSI reference method. Among these blood samples, about 75% have a white blood cell concentration equal or higher than $11 \times 10^3/\mu L$.

FIG. 6 shows the correlation of the apparent hemoglobin concentration (Apparent Hgb) of these blood samples obtained on the hematology analyzer with the reference hemoglobin concentration (Reference Hgb) obtained using the reference method. FIG. 7 shows the correlation of the corrected hemoglobin concentration (corrected Hgb) obtained using equation 2 with the reference hemoglobin concentration of these blood samples.

Similarly, FIG. 8 shows the correlation of the corrected hemoglobin concentration obtained using equation 5 with the reference hemoglobin concentration. FIG. 9 shows the correlation of the corrected hemoglobin concentration obtained using equation 8 with the reference hemoglobin concentration.

As shown, after correction using equation 2, 5, or 8, the obtained corrected hemoglobin concentration of these samples have an excellent correlation with the reference hemoglobin concentration, which is improved from the correlation of the apparent hemoglobin concentration with the reference hemoglobin concentration. As can be observed from the correlation graphs, after correction those scattered data points shown in FIG. 6, caused by interference of high white blood cell concentration in the samples, become consistent with the results provided from the reference method.

As described above, the concentration of the cellular particles in the sample mixture used for hemoglobin measurement is determined by measuring the particles above the detection threshold of the particle measurement device. It has been found that smaller particles, which fall below the detection threshold, in most cases do not cause interference to the hemoglobin measurement. As discussed above, the smaller the cellular particles are, the less interference they cause. Moreover, these smaller particles, in which most are small fragments of cellular debris and platelets, are not nucleated cells, and they scatter less than the nucleated cells. However, when a blood sample has an extremely high concentration of platelets, such as above $700 \times 10^3/\mu L$, the platelets in the sample mixture can interfere with the hemoglobin measurement. In this situation, platelet concentration obtained from a separate measurement on the hematology analyzer, as described later, can be used for correction of its contribution to the apparent hemoglobin concentration.

As can be understood, for platelets the predetermined criterion can be substantially different from the predetermined criterion for white blood cells and other particles having a similar size. Therefore, in another embodiment, the method of the present invention further includes comparing the obtained concentrations of different types of cellular particles to different predetermined criteria, and only when the concentration of one type of cellular particles exceeds its corresponding predetermined criterion, then initiating the correction process for this type of cellular particles. For example, the method can include two predetermined criteria, one for white blood cells and other particles having a similar size, and another for platelets. In one exemplary embodiment, the former is set at $11 \times 10^3/\mu L$ and the latter is set at $700 \times 10^3/\mu L$.

The method of correcting particle interference to hemoglobin measurement as described above in several embodiments of the present invention can be implemented on a hematology analyzer and can be performed in an automated process. More specifically, the process comprises (a) passing a first sample mixture portion through a light path, measuring absorbance of the first sample mixture portion at a predetermined wavelength of a hemoglobin chromogen formed in the first sample mixture portion to obtain an apparent hemoglobin concentration of the blood sample, and storing the apparent hemoglobin concentration in a first memory; (b) passing a second sample mixture portion through a particle measurement device, counting number of cellular particles in the second sample mixture portion to obtain concentration of the cellular particles, and storing the concentration in a second memory; (c) determining a contributory hemoglobin equivalence using the concentration and a function of size of the particles; (d) removing obtained contributory hemoglobin equivalence from the apparent hemoglobin concentration to obtain a corrected hemoglobin concentration of the blood sample; and (e) reporting the corrected hemoglobin concentration of the blood sample.

Herein, the term "function of size of the cellular particle" includes the size factor ($S_f$) defined above, and the average light extinction efficiency factor of the particles as shown in equations 19 and 20. It should be understood that the average light extinction efficiency factor is a part of $\beta_V$, $\beta_A$, and $\beta_D$ in equations 2, 5 and 8, a part of $\beta_1$, $\beta_2$, $\beta_3$, and $\beta_j$ in equation 22, and a part of $\gamma_1$, $\gamma_2$, $\gamma_3$, and $\gamma_j$ in equation 23, respectively. The first memory and second memory refer to two memory locations of a computer system on the hematology analyzer, designated for storing data received from the measurements described above.

In one embodiment, the first sample mixture portion and the second sample mixture portion are prepared together by mixing one aliquot of a blood sample with a lytic reagent to lyse red blood cells for both hemoglobin and white blood cell measurements. In other words, the first sample mixture portion and the second sample mixture portion can be two segments of one sample mixture. Depending on the flow arrangement on the instrument, the two portions may also partially overlap, for example, in sequential measurements performed in a shared flow path. As can be appreciated from the embodiments described above, concentration and size of the cellular particles in one sample mixture, which is used for both hemoglobin measurement and white blood cell measurement, can be measured and used for correcting interference of the cellular particles to the hemoglobin measurement. In many hematology analyzers, such a joint sample preparation and concurrent measurements are available. Therefore, the method of the present invention described in several embodiments above can be conveniently implemented on these hematology analyzers as an automated process.

In an alternative embodiment, the two sample mixture portions are prepared separately. More specifically, the first sample mixture portion is prepared by mixing a first aliquot of the blood sample with a first lytic reagent to lyse red blood cells therein, and the second sample mixture portion is prepared by mixing a second aliquot of the blood sample with a second lytic reagent to lyse red blood cells therein. In this situation, the first sample mixture portion and the second sample mixture portion may have different dilution ratios and different chemical reactions. With this embodiment, the relationship of cellular particle contribution to the apparent hemoglobin concentration in the first sample mixture can be determined experimentally using equation 21 to obtain the empirical constant γ. As discussed previously, γ is a function of the size and reflective index of the particles. Once this constant is determined, corrected hemoglobin concentration of a blood sample can be obtained according to equation 20, where the apparent hemoglobin concentration (AHgb) is measured from the first sample mixture portion and the cellular particle concentration $C_p$ is measured from the second sample mixture portion.

It is known that several existing hematology analyzers have separate hemoglobin and white blood cell measurements. Therefore, the process of this embodiment can be implemented on these analyzers. Typically, the white blood cell measurement involves differentiation of white blood cell subpopulations based on size distribution in one, two, or three dimensions. However, because of a different chemical reaction in the second sample mixture portion, size distribution observed in the measurement of the second sample mixture portion does not necessarily represent that present in the first sample mixture portion. If the size distributions are different, only concentration of white blood cells obtained from the second sample mixture portion is used for correcting the particle interference to hemoglobin measurement using equation 20.

As can be understood, the interference of platelets to hemoglobin measurement of a blood sample having an abnormally high platelet concentration can also be corrected using equation 20. In this case, the empirical constant γ specific to platelets can be determined using equation 21, using clinical blood samples having abnormally high platelet concentrations, using whole blood samples with addition of platelets harvested from human whole blood, or using suitable platelet analogs. Once the empirical constant γ is determined, corrected hemoglobin concentration of a blood sample can be obtained according to equation 20, where the apparent hemoglobin concentration (AHgb) is measured from the first sample mixture portion and the platelet concentration is obtained from the second sample mixture portion, which is prepared by mixing an aliquot of the blood sample with a diluent and is used to measure platelets (may also include a measurement of red blood cells) as described herein later.

In the embodiments described above, the particle interference to hemoglobin measurement is corrected using equations expressed by hemoglobin concentration. Alternatively, the equations can also be expressed using absorbance, instead of hemoglobin concentration of the blood sample. As can be appreciated, according to the Beer-Lambert law the absorbance of a sample mixture is linearly proportional to hemoglobin concentration in the sample mixture. In this approach, equations 2, 5, 8, and 20 described above can be modified and expressed using corrected absorbance and apparent absorbance, where the particle concentration ($C_p$) and size factor ($S_f$) remain the same, but the conversion factor will be different. Using this approach, the corrected hemoglobin is then calculated from the obtained corrected absorbance. It is further noted that in this approach the contributory hemoglobin equivalence can be expressed equivalent to absorbance, instead of equivalent to concentration as it is in the embodiments described above.

As a further aspect of the present invention, using the corrected hemoglobin concentration obtained by the method of the present invention, particle interference to other derivative parameters, such as mean corpuscular hemoglobin (MCH) and mean corpuscular hemoglobin concentration (MCHC), can also be corrected. On automated hematology analyzers, MCH and MCHC are derived from other directly measured parameters, more specifically from red blood cell concentration (RBC), mean cell volume (MCV) and hemoglobin concentration. Herein, MCH=Hgb/RBC*10; and MCHC=(Hgb/(RBC*MCV))*1000.

In this embodiment, the method described above further comprises: mixing another aliquot of the blood sample with a diluent to form another sample mixture; measuring concentration and mean cell volume of red blood cells in the another sample mixture; obtaining a corrected mean corpuscular hemoglobin (MCH) using the corrected hemoglobin concentration obtained using the method of the present invention and the obtained concentration of the red blood cells; and obtaining a corrected mean corpuscular hemoglobin concentration (MCHC) using the corrected hemoglobin concentration, and the concentration of the red blood cells and the mean cell volume.

Methods of measuring red blood cell concentration and mean cell volume are known in the art. For measuring the red blood cells a blood sample is typically diluted substantially with a diluent in a sample chamber or bath. Using an impedance measurement with a non-focused flow aperture, the blood sample can be diluted with a dilution ratio of about 6250:1. When a focused-flow flowcell is used for the measurement, the dilution ratio can be substantially lower, such as 290:1. To maintain red blood cell volume and morphology during their measurements on a hematology analyzer, an isotonic diluent is used for diluting the blood sample. Various commercially available isotonic blood diluents can be used for diluting the blood sample. Suitable examples include, but are not limited to, the diluents described in U.S. Pat. Nos. 4,521,518, 4,528,274, 5,935,857, and 6,706,526.

The DC impedance measurement described above in the measurement of white blood cell concentration and size distribution can be used for measuring red blood cells to obtain the concentration (RBC) and mean cell volume (MCV) of the red blood cells of a blood sample. Moreover, concentration and size of platelets are also measured concurrently with red blood cells in the same sample mixture, and they are distinguished from the red blood cells based on the size difference. Alternatively, RBC, MCV, and platelet concentration can also be obtained using light scatter measurement of said another sample mixture.

Then, using the corrected hemoglobin concentration obtained with the method of the present invention described above, and the RBC and MCV obtained from the measurement of said another sample mixture (the second sample mixture), the corrected MCH and MCHC are obtained. In the corrected MCH and MCHC, the contribution of the cellular particles in the sample mixture used for hemoglobin measurement (the first sample mixture) to the apparent hemoglobin concentration is removed.

However, it is also known that white blood cells, when present in very high concentration in a blood sample, for example more than 50×10³/µL, can also cause interference to the measurement of red blood cell concentration and mean cell volume. This can also result in error in the reported MCH and MCHC on the hematology analyzer.

In a further embodiment, the present invention further provides correction of interference of white blood cells to MCH and MCHC due to their interference to the red blood cell measurement, or the measurement of the second sample mixture. The correction processes have been described in detail in U.S. Pat. No. 7,482,165, which is hereby incorporated by reference in its entirety. These correction processes correct interference of white blood cells to red blood cell concentration (RBC) and mean cell volume (MCV).

As can be appreciated, after performing a double correction (i.e., in the measurements of the first and the second sample mixtures), all directly measured parameters, i.e., Hgb, RBC and MCV, used for deriving MCH and MCHC are corrected. As such, the accuracy of MCH and MCHC of blood samples having a very high white blood cell concentration can be substantially improved.

As described, the method of the present invention can be conveniently implemented on existing hematology analyzers, utilizing existing measurement devices for hemoglobin, white blood cell, red blood cell, and platelet measurements and the data obtained from these measurements to correct the interference of cellular particles to hemoglobin measurement. Such implementation does not require new hardware, and does not require change of existing instrument structure or measurement processes. Therefore, the method of the present invention provides the ability of correcting particle interference to hemoglobin measurement and improvements to accuracy of hemoglobin concentration, MCH, and MCHC, without additional manufacturing cost.

As can be further appreciated, using the method of the present invention pre-dilution of high white blood cell samples is no longer required. This eliminates the time consuming and error prone manual dilution process, and improves the accuracy in measuring high white blood cell or high platelet samples by eliminating inherent errors introduced by manual dilution.

The following examples are illustrative of the invention and are in no way to be interpreted as limiting the scope of the invention, as defined in the claims. It will be understood that various other ingredients and proportions may be employed, in accordance with the proceeding disclosure.

Example 1

An experimental hematology analyzer, which included a WBC chamber equipped with a DC impedance detector and a hemoglobin measurement device having a cuvette fluidly connected to the WBC chamber, was used for analysis of the blood samples of interest. The hemoglobin measurement device included a light source projecting a light on the cuvette and a light detector detecting the light transmitted through the cuvette at about 540 nm. Transmitted light was used to calculate hemoglobin concentration of the blood sample being measured. The hematology analyzer also included a RBC chamber equipped with another DC impedance detector for measuring red blood cells and platelets using DC impedance measurements. Each of WBC chamber and RBC chamber has three non-focused flow apertures. The hematology analyzer measures concentration and size of white blood cells and red blood cells in a blood sample by DC impedance measurements.

In measuring hemoglobin and white blood cells, a first aliquot of about 28 µl of a blood sample was diluted with about 6 ml of an isotonic diluent (D×H Diluent, product of Beckman Coulter, Inc., Fullerton, Calif.), and then mixed with about 1.08 ml of a lytic reagent (D×H Cell Lyse, product of Beckman Coulter, Inc., Fullerton, Calif.) in the WBC chamber to form a first sample mixture, with a total dilution ratio of the reagents to the blood of about 250:1. The red blood cells in the first sample mixture were lysed and the released hemoglobin formed a chromogen with its maximum absorption at about 540 nm. The first sample mixture was then caused to pass through the apertures by a vacuum source and to pass the cuvette. As the cellular particles, mainly white blood cells, passed through the apertures, the number of the particles were counted and the size of the particles were measured using a channelizer of the DC detector. The absorption of the first sample mixture was measured in the cuvette, and was used to calculate hemoglobin concentration (which was the apparent hemoglobin concentration (AHgb) as defined for the purpose of the present invention). The number of particles counted in the first sample mixture was used to calculate the white blood cell concentration of the blood. The electrical pulses received in the channelizer were used to produce a white blood cell distribution histogram, which was used to perform a 3-part differential analysis, differentiating white blood cells into lymphocytes, monocytes and granulocytes.

Concurrently, a second aliquot of about 1.6 µl of the blood sample was diluted by about 10 ml of the D×H Diluent in the RBC chamber with a dilution ratio of about 6250:1 to form a second sample mixture. The second sample mixture was caused to pass through the apertures in the RBC chamber, numbers of red blood cells and platelets were counted and the sizes of these cells were measured using a channelizer of the DC detector. The obtained numbers of red blood cells and platelets were used to calculate concentrations of the red blood cells (RBC) and platelets (PLT), respectively. The signals received in the channelizer were used to produce a red blood cell distribution histogram, which was used to determine mean cell volume (MCV) of the red blood cells.

Then, the hemoglobin concentration (AHgb) obtained from the measurement of the first sample mixture and RBC and MCV obtained from the measurement of the second sample mixture were used to calculate MCH and MCHC.

143 whole blood samples were collected from four hospitals and analyzed on two of the experimental hematology analyzers described above. Among these samples, 107 samples had white blood cell concentration higher than $11 \times 10^3/\mu L$. Hemoglobin concentration of these samples was also measured using CLSI reference method, and the results were referred to as the reference hemoglobin concentration. Using the reference method, all blood samples that had the absorbance ratio<1.59 or the absorbance at 750 nm$\geq$0.003 were filtered by a 0.2 µm filter. FIG. 1 shows a white blood cell distribution histogram of one normal blood sample obtained on the experimental hematology analyzer.

FIG. 6 shows the correlation of the apparent hemoglobin concentration of these blood samples obtained on the hematology analyzer with the reference hemoglobin concentration (Reference Hgb) obtained using the reference method. FIG. 2 further shows the difference between the apparent hemoglobin concentration and the reference hemoglobin concentration of these blood samples versus the concentration of the cellular particles obtained from the first sample mixture. It is noted that the total cellular particle concentration here is expressed using the particle concentration in a whole blood sample after considering the dilution, and it is also referred to as raw WBC. As shown, because a large number of these blood samples had a white blood cell concentration above $11 \times 10^3/\mu L$, substantially elevated apparent hemoglobin concentrations were observed caused by particle interference. 3-part differential results of 8 blood samples having a white blood cell concentration above $120 \times 10^3/\mu L$ are shown in the table in FIG. 2.

The obtained apparent hemoglobin concentration from the experimental hematology analyzers, the total cellular particle concentration ($C_p$) obtained from the measurement of the first sample mixture, and the list mode data of the pulse signals obtained from the channelizer were post analyzed using the method of the present invention to obtain corrected hemoglobin concentration.

FIG. 7 shows the correlation of the corrected hemoglobin concentration (Corrected Hgb) obtained using equation 2 with the reference hemoglobin concentration of these blood samples. Here, in equation 2, $V_m$ was the weighted mean volume of the cellular particles measured in each sample, calculated using equation 3 using the data received from the channelizer. $\beta_v$ was obtained based on the relationship shown in equation 4, and it was the slope of the linear regression curve of the difference between the apparent and the reference hemoglobin concentrations and $C_p*V_m$. As shown, the corrected hemoglobin concentration had an excellent correlation with the reference hemoglobin concentration, which was improved from the correlation of the apparent hemoglobin concentration with the reference hemoglobin concentration.

FIG. 8 shows the correlation of the corrected hemoglobin concentration obtained using equation 5 with the reference hemoglobin concentration. Here, in equation 5, $A_m$ was the weighted mean cross-section area of the cellular particles measured in each sample, calculated using equation 6 using the data received from the channelizer. $\beta_A$ was obtained based on the relationship shown in equation 7, and it was the slope of the linear regression curve of the difference between the apparent and the reference hemoglobin concentrations and $C_p*A_m$ as shown in FIG. 5A. As shown in FIG. 7, the corrected hemoglobin concentration obtained using equation 5 also had an excellent correlation with the reference hemoglobin concentration.

FIG. 9 shows the correlation of the corrected hemoglobin concentration obtained using equation 8 with the reference hemoglobin concentration. Here, in equation 8, $D_m$ was the weighted mean diameter of the cellular particles measured in each sample, calculated using equation 9 using the data received from the channelizer. $\beta_D$ was obtained based on the relationship shown in equation 10, and it was the slope of the linear regression curve of the difference between the apparent and the reference hemoglobin concentrations and $C_p*D_m$ as shown in FIG. 5B. As shown in FIG. 8, the corrected hemoglobin concentration obtained using equation 8 also had an excellent correlation with the reference hemoglobin concentration.

Example 2

Two cellular analogs were used together a normal fresh whole blood sample to prepare two series of test samples to simulate high white blood cell samples having different sizes of white blood cells. The whole blood sample had hemoglobin concentration of 13.99 g/dL and WBC of $9.73\times10^3/\mu L$ as reported on a Beckman Coulter LH750 hematology analyzer (product of Beckman Coulter, Inc., Fullerton, Calif.). Hemoglobin and white blood cell measurements on LH750 hematology analyzer were performed using the same detection mechanisms described in Example 1, using Lyse S III diff and Isoton 3E as the lytic reagent and the diluent, respectively (both reagents were product of Beckman Coulter, Inc., Fullerton, Calif.). The LH750 hematology analyzer was calibrated and operated under the standard operation condition recommended by the manufacturer.

The first cellular analog was made of fixed human red blood cells, which was used as an analog to simulate lymphocytes in reference control product, hence, referred to as lymphocyte analog. The second cellular analog was made of fixed alligator whole blood, which was used as an analog to simulate granulocytes in reference control product, hence, referred to as granulocyte analog.

2 ml of the whole blood sample was added into each of 9 test tubes, and then predetermined volumes of the lymphocyte analog suspension was added into these test tubes in increasing order, which produced the first series of test sample with lymphocyte analog concentration from 0 to $500\times10^3/\mu L$. Similarly, second series of 9 test samples were prepared using the granulocyte analogs having the granulocyte analog concentration from 0 to $500\times10^3/\mu L$.

Each of these two series of test samples was analyzed on the LH750 hematology analyzer in the same manner of analyzing a blood sample. The apparent hemoglobin concentrations reported on the analyzer were plotted against the analog concentrations in the test samples, as shown in FIG. 4.

In FIG. 4, the Y-axis is the apparent hemoglobin concentration and the X-axis is the concentration of the analogs in the test samples. The data points expressed by the solid symbols (along the top two lines) were the apparent hemoglobin concentration reported on the analyzer. The data points expressed by the hollow symbols were the theoretical hemoglobin concentrations calculated according to the degree of dilution caused by addition of the analog suspension. The theoretical concentrations were further confirmed by preparing a further set of test samples, with addition of only the liquid medium to the whole blood, in the same increasing order, without including the cellular analogs.

As shown, within each set of test samples, the apparent hemoglobin concentration increased with the increase of the analog concentration. Moreover, the apparent hemoglobin concentrations were substantially higher in the test samples containing the granulocyte analogs than those containing the lymphocyte analogs.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method of correction of particle interference to hemoglobin measurement of a blood sample comprising:
    (a) mixing an aliquot of a blood sample with a lytic reagent to lyse red blood cells, and forming a sample mixture;
    (b) measuring absorbance of said sample mixture at a predetermined wavelength of a hemoglobin chromogen formed in said sample mixture, and obtaining an apparent hemoglobin concentration of said blood sample using obtained absorbance;

(c) measuring a first concentration and a first size of a first subpopulation of cellular particles of a first type remaining in said sample mixture;

(d) measuring a second concentration and a second size of a second subpopulation of cellular particles of a second type remaining in said sample mixture;

(e) determining a corrected hemoglobin concentration of said blood sample by removing a contribution of said first and second subpopulations of cellular particles to said apparent hemoglobin concentration, the determining based on at least said first measured concentration, said first measured size, a first size factor, said second measured concentration, said second measured size, and a second size factor, said first and second size factors being different from each other, the first size factor being based, at least in part, on the shape of particles of the first type, the second size factor being based, at least in part, on the shape of particles of the second type; and (f) reporting said corrected hemoglobin concentration of said blood sample.

2. The method of claim 1, wherein said sizes are defined by mean volumes of said respective subpopulations of cellular particles in said sample mixture.

3. The method of claim 2, wherein said mean volume of said cellular particles comprises at least one of weighted mean volume, geometric mean volume, mode volume or median volume, determined from a size distribution of said cellular particles.

4. The method of claim 2, wherein said sizes are defined by mean cross-section area of said respective subpopulations of said cellular particles in said sample mixture.

5. The method of claim 4, wherein said mean cross-section area of said cellular particles comprises at least one of weighted mean cross-section area, geometric mean cross-section area, mode cross-section area, or median cross-section area, determined from a size distribution of said cellular particles.

6. The method of claim 1, wherein said sizes are defined by a mean diameter of said respective subpopulations of said cellular particles in said sample mixture.

7. The method of claim 6, wherein said mean diameter of said cellular particles comprises at least one of weighted mean diameter, geometric mean diameter, mode diameter or median diameter, determined from a size distribution of said cellular particles.

8. The method of claim 1, wherein said sizes are defined by one or more members of the group consisting of mean volume, mean cross-section area, mean diameter of said respective subpopulations of cellular particles in said sample mixture and combinations thereof.

9. The method of claim 1, wherein said concentrations and said sizes of said subpopulations of cellular particles are measured by DC impedance measurement.

10. The method of claim 1, wherein said concentrations and said sizes of said subpopulations of cellular particles are measured by a light scatter measurement.

11. The method of claim 1, wherein said predetermined wavelength is selected from 380 nm-770 nm, inclusive.

12. The method of claim 1, wherein said predetermined wavelength is at about 540 nm.

13. The method of claim 1, wherein said cellular particles comprise white blood cells, nucleated red blood cells, platelets, giant platelets, platelet clumps, unlysed red blood cells, or cellular debris.

14. The method of claim 1 further comprising prior to (e), comparing an overall concentration of cellular particles to a predetermined criterion; and when said overall concentration of cellular particles exceeds said predetermined criterion, then initiating (e).

15. The method of claim 1 further comprising:

(g) mixing another aliquot of said blood sample with a diluent to form another sample mixture;

(h) measuring concentration and mean cell volume of red blood cells in said another sample mixture;

(i) obtaining a corrected mean corpuscular hemoglobin (MCH) using said corrected hemoglobin concentration obtained in (e) and said concentration of said red blood cells obtained in (h); and (j) obtaining a corrected mean corpuscular hemoglobin concentration (MCHC) using said corrected hemoglobin concentration obtained in (e), said concentration of said red blood cells and said mean cell volume obtained in (h).

16. The method of claim 1, wherein each size factor represents a deviation of the respective type of cellular particle from an ideal sphere.

17. An automated process for correction of particle interference to hemoglobin measurement of a blood sample on a hematology analyzer comprising:

(a) passing a first portion of said blood sample through a light path, measuring absorbance of said first portion of said blood sample at a predetermined wavelength of a hemoglobin chromogen formed in said first portion of said blood sample to obtain an apparent hemoglobin concentration of said blood sample, and storing said apparent hemoglobin concentration in a first memory;

(b) passing a second portion of said blood sample through a particle measurement device, counting a first number of a first subpopulation of a first type of cellular particles in said second portion of said blood sample to obtain a first concentration of said first type cellular particles, counting a second number of a second subpopulation of a second type of cellular particles in said second portion of said blood sample to obtain a second concentration of said second type cellular particles, and storing said first and second concentrations in a second memory;

(c) determining a corrected hemoglobin concentration of said blood sample by removing a contribution of said first and second subpopulations of cellular particles to said apparent hemoglobin concentration, the determining based at least in part on said first and second concentrations and a first size factor of said first type of cellular particles and a second size factor of said second type of cellular particle, said first and second size factors being different from each other, the first size factor being based, at least in part, on the shape of the first type of cellular particles, the second size factor being based, at least in part, on the shape of the second type of cellular particles;

(d) reporting said corrected hemoglobin concentration of said blood sample.

18. The process of claim 17, wherein said first portion of said blood sample and said second portion of said blood sample are prepared together by mixing one aliquot of said blood sample with a lytic reagent to lyse red blood cells therein.

19. The process of claim 17, wherein said first portion of said blood sample is prepared by mixing a first aliquot of said blood sample with a first lytic reagent to lyse red blood cells therein, and said second portion of said blood sample is prepared by mixing a second aliquot of said blood sample with a second lytic reagent to lyse red blood cells therein.

20. The process of claim 17, wherein said first portion of said blood sample is prepared by mixing a first aliquot of said blood sample with a first lytic reagent to lyse red blood cells therein, and said second portion of said blood sample is prepared by mixing a second aliquot of said blood sample with a diluent.

21. The process of claim 17 further comprising prior to (c), comparing an overall concentration of said cellular particles to a predetermined criterion, and when said overall concentration of said cellular particles exceeds said predetermined criterion, then initiating (c).

22. The process of claim 17, wherein said first type of particle and said second type of particles are each chosen from the group consisting of white blood cells, nucleated red blood cells, platelets, giant platelets, platelet clumps, unlysed red blood cells, or cellular debris.

23. The process of claim 17, wherein each size factor represents a deviation of the respective type of cellular particles from an ideal sphere.

\* \* \* \* \*